(12) United States Patent
Velayudhan et al.

(10) Patent No.: US 9,850,285 B2
(45) Date of Patent: Dec. 26, 2017

(54) PROCESS FOR PREPARING EPTIFIBATIDE

(71) Applicant: Laurus Labs Limited, Hyderabad (IN)

(72) Inventors: Subha Nair Velayudhan, Hyderabad (IN); Ravindra Babu Bollu, Hyderabad (IN); Venkata S. Indukuri, Hyderabad (IN); Seeta R. Gorantla, Hyderabad (IN); Venkata S. Kallam, Hyderabad (IN); Bala M. Madivada, Hyderabad (IN)

(73) Assignee: LAURUS LABS LIMITED, Andhra, Pradesh (IN)

( * ) Notice: Subject to any disclaimer, the term of this patent is extended or adjusted under 35 U.S.C. 154(b) by 0 days.

(21) Appl. No.: 14/842,332

(22) Filed: Sep. 1, 2015

(65) Prior Publication Data
US 2016/0017002 A1   Jan. 21, 2016

Related U.S. Application Data

(63) Continuation of application No. 14/235,349, filed as application No. PCT/IB2012/001444 on Jul. 26, 2012, now Pat. No. 9,156,885.

(30) Foreign Application Priority Data

Jul. 27, 2011 (IN) .................. 2573/CHE/2011
Sep. 12, 2011 (IN) .................. 3119/CHE/2011

(51) Int. Cl.
| | |
|---|---|
| *C07K 7/64* | (2006.01) |
| *C07K 7/06* | (2006.01) |
| *C07K 5/08* | (2006.01) |
| *C07K 5/10* | (2006.01) |
| *C07K 5/06* | (2006.01) |
| *A61K 38/00* | (2006.01) |

(52) U.S. Cl.
CPC .................. *C07K 7/64* (2013.01); *C07K 5/06* (2013.01); *C07K 5/08* (2013.01); *C07K 5/10* (2013.01); *C07K 7/06* (2013.01); *A61K 38/00* (2013.01)

(58) Field of Classification Search
None
See application file for complete search history.

(56) References Cited

U.S. PATENT DOCUMENTS

2014/0163203 A1* 6/2014 Velayudhan et al. ......... 530/329

FOREIGN PATENT DOCUMENTS

| | | | |
|---|---|---|---|
| CN | 1500805 | * | 6/2004 |
| CN | 1222537 | * | 10/2005 |
| CN | 101747412 | * | 6/2010 |
| CN | 101993475 | * | 3/2011 |
| CN | 102040652 | * | 3/2011 |
| IN | 200801402 I4 | * | 12/2009 |

OTHER PUBLICATIONS

International Search Report dated Dec. 20, 2012; International Application No. PCT/IB2012/001444; International Filing Date: Jul. 26, 2012; 5 pages.
Written Opinion dated Dec. 20, 2012; International Application No. PCT/IB2012/001444; International Filing Date: Jul. 26, 2012; 4 pages.

* cited by examiner

*Primary Examiner* — Maury Audet
(74) *Attorney, Agent, or Firm* — Blank Rome LLP

(57) ABSTRACT

The present invention provides processes for preparation of eptifibatide that involve coupling of amino acids in a (2+5), (4+3) and (3+4) sequence method. The invention further provides products produced by the described processes, novel compounds that can be used as synthetic intermediates for the preparation of eptifibatide.

7 Claims, No Drawings

PROCESS FOR PREPARING EPTIFIBATIDE

PRIORITY

This application is a continuation of U.S. application Ser. No. 14/235,349, filed Jul. 26, 2012, which is a U.S. National Phase of PCT/IB2012/001444, filed Jul. 26, 2012, which claims the priority of Indian Provisional Application Nos. 2573/CHE/2011, filed Jul. 27, 2011, and 3119/CHE/2011, filed Sep. 12, 2011, the contents of each of which are incorporated herein by reference herein.

FIELD OF THE INVENTION

The present invention generally relates to novel processes for preparing eptifibatide. The invention also relates to processes for synthetic intermediates for eptifibatide, and to processes for purifying eptifibatide.

BACKGROUND OF THE INVENTION

Eptifibatide, also known as $N^6$-(aminoiminomethyl)-$N^2$-(3-mercapto-1-oxopropyl-L-lysylglycyl-L-α-aspartyl-L-tryptophyl-L-prolyl-L-cysteinamide, cyclic (1-6) disulfide, is a highly specific cyclic heptapeptide antagonist of the platelet glycoprotein IIb/IIIa used for the treatment of cardio vascular disease, is represented by the following Formula I.

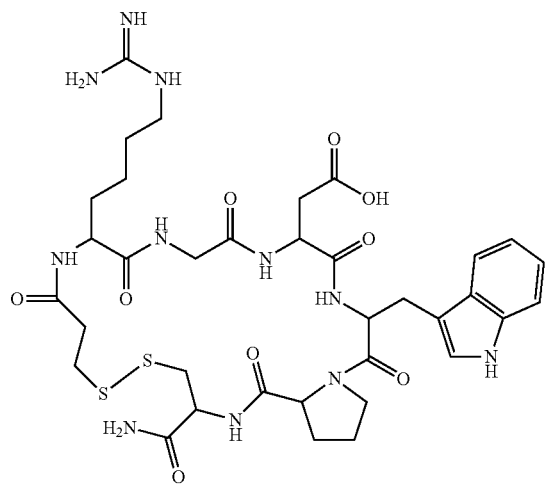

Formula I

Eptifibatide is a short acting parenteral antithrombotic agent that is used for treating Acute Coronary Syndrome (ACS). It is also used in patients undergoing Percutaneous Coronary Intervention (PCI). Eptifibatide is a platelet aggregation inhibitor (PAI) and belongs to a new class of RGD mimetics-arginine (R), glycine (G), esparto acid (D). Eptifibatide reversibly inhibits platelet aggregation by preventing the binding of fibrinogen, von Willebrand factor and other adhesive ligands to the GP IIb/IIIa receptors.

Eptifibatide is marketed in the United States under the brand name of INTEGRILIN®, and is used to treat patients with acute coronary syndrome (unstable angina and non-Q-wave MI), including patients who are to be managed medically and those undergoing PCI. Integrilin is intended for use with acetylsalicyclic acid and unfractionated heparin.

In terms of peptide synthesis methodology, two major synthetic techniques dominate current practice. These are synthesis in solution phase and synthesis on solid phase. The solution phase synthesis has generally been viewed as more feasible than solid phase synthesis for the large scale manufacture of eptifibatide.

Alternatively, selected polypeptides are produced by expression of recombinant DNA constructs. The DNA encoding the sequenced polypeptide is prepared using commercially available nucleic acid synthetic method. Production by recombinant method is particularly preferred for peptides of at least 8 amino acid residues. U.S. Pat. Nos. 5,318,899 and 5,958,732 discloses recombinant techniques to synthesize eptifibatide; the lysine residue is converted to homoarginine residue by solution phase synthesis. WO 2005/121164 and US 2007/249806, disclose the synthesis of peptide on a solid support resin, and subsequently modifying by solution phase synthesis for conversion of lysine residue to homoarginine residue, through guanylation with 3,5-dimethyl pyrazole-1-carboxamide nitrite.

In solid phase peptide synthesis, the desired peptide is prepared by the step-wise addition of amino acid moieties to a building peptide chain. The two most widely used protocols, in solid-phase synthesis, employ tert-butyloxycarbonyl (Boc) or 9-fluorenylmethoxycarbonyl (Fmoc) as amino protecting groups. Many of the reported synthetic approaches to eptifibatide have employed known techniques of solid phase peptide synthesis, mainly, using Boc-chemistry, as described, for example, in U.S. Pat. No. 5,318,899, U.S. Pat. No. 5,686,570, U.S. Pat. No. 5,747,447, U.S. Pat. No. 5,759,999, U.S. Pat. No. 576,333, U.S. Pat. No. 5,770,564, U.S. Pat. No. 5,807,825 and U.S. Pat. No. 5,851,839. Fmoc based solid phase synthesis are described in WO2005/121164, WO2003/093302, CN1858060A, CN1500805A, WO2006045483, WO2006119388, WO2003093302 and US 2007249806. For the synthesis of cyclic peptide, the linear peptide conveniently prepared on resin is cleaved from the support followed by cyclization in solution.

However, as with many peptides the major challenge with eptifibatide is to produce sufficiently pure material at an acceptable cost. A commercial scale solution phase synthesis was reported at the 1999 IBC conference on peptide technologies, "Peptisyntha's method of producing GMP peptides on an Industrial scale". The commercial scale solution phase involves a convergent synthesis, where the two fragments, Mpr-Har-Gly and Asp-Trp-Pro, are coupled to provide six of the seven residues needed for eptifibatide. The last residue attached is S-trityl-cysteinamide, as described, for example, in U.S. Pat. No. 5,506,362. After removal of the S-trityl protecting groups (on cysteinamide and mercaptopropionyl residues), and subsequent intramolecular cyclization via di-sulphide bond formation afforded crude eptifibatide with reported purity of about 80%. Two column purifications improve the purity to greater than 99%.

U.S. Pat. No. 7,674,768 ("the '768 patent") discloses a (1+6) solution phase synthesis for the preparation of eptifibatide by first preparing the fragment of Har-Gly-Asp-Trp-Pro-Cys(NH$_2$)—S—S-Mpr-OH and then coupling the Har with the Mpr, to yield crude eptifibatide with a purity of about 46%. The crude eptifibatide on primary preparative column purification with trifluoroacetic acid/acetonitrile-based system and then secondary preparative column purification with acetic acid/acetonitrile based system gives pure eptifibatide with a purity of 99%. The synthesis disclosed in the '768 patent is schematically represented as follows:

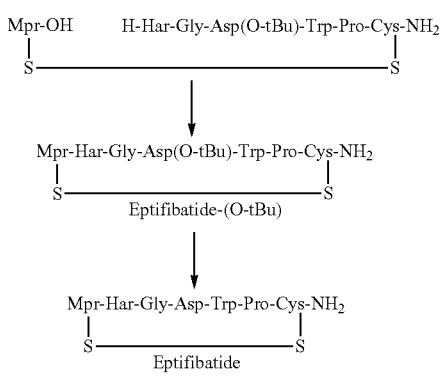

The '768 patent discloses multiple use of highly expensive chromatography technique such as preparative column chromatography to improve the purity of the resultant crude eptifibatide; which in turn result to an increase in the consumption of chromatography eluents and manufacturing cycle time, this leads to decrease in the product yield and manifold increase in production cost.

Patent publication WO2011079621 ("the '621 publication") discloses a (3+4) solution phase synthesis for the preparation of eptifibatide by separate preparation of two protected fragments Mpr-Har-Gly-OH and Asp-Trp-Pro-Cys-NH$_2$. The coupling of these two fragments provides protected linear peptide; the protected groups are removed and subsequent intramolecular ring closure by disulfide bond formation afforded crude eptifibatide with a purity of about 84%. The crude eptifibatide on preparative column purification with trifluoroacetic acid/acetonitrile-based system and then freeze drying gives the pure eptifibatide trifluoroacetate with a purity of 99.14% and contains about 0.17%, 0.29% and 0.22% of closely related impurities. The synthesis disclosed in the '621 publication is schematically represented as follows:

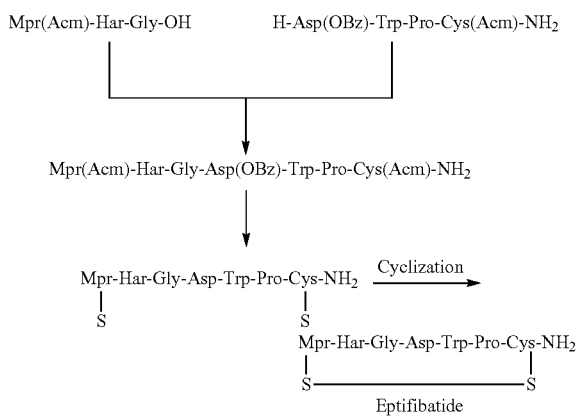

The '621 publication has the following disadvantages, such as:
i) The product, eptifibatide trifluoroacetate salt obtained after preparative purification requires additional process steps such as another preparative purification to make pharmaceutically acceptable eptifibatide acetate salt,
ii) The benzyl group deprotection at -Asp is carried out with hydrogen atmosphere in presence of palladium on carbon. The use of palladium for the debenzylation in sulphur containing compounds lead to insufficient conversion due to sulphur poisoning of the catalyst,
iii) It doesn't mention the content of isomeric impurities present/formed during the synthesis of the intermediates and the linear peptide, and
iv) The presence of closely related impurities is above the acceptable level recommended by the regulatory authorities.

U.S. Patent publication No 2006/0276626 ("the '626 publication") discloses a process for the preparation of eptifibatide by first hexamer [Mpr-Har-Gly-Asp-Trp-Pro] was synthesized by solid phase synthesis using super acid labile resin and then introducing the Cys-NH$_2$ by a solution phase synthesis, to yield crude eptifibatide. The crude eptifibatide on preparative column purification with trifluoroacetic acid system gives eptifibatide trifluoroacetate at a purity of 98.5% and then secondary preparative column purification for counter-ion exchange followed by lyophilization gives pure eptifibatide with a purity of 99%.

PCT publication WO 2009/150657 ("the '657 publication") discloses a process for preparation of eptifibatide by using Fmoc solid phase synthesis. The '657 publication also discloses a purification process of crude eptifibatide by using preparative chromatography followed by salt exchange.

PCT publication WO 2004/092202 ("the '202 publication") discloses a process for purification of eptifibatide by repeated purifications using preparative chromatography and then lyophilization.

It is known that purity and yield of the peptide are important aspects of any route of synthesis. Purity is represented by the degree of presence of pharmacologically active impurities, which though present in trace amounts only, may disturb or even render useless the beneficial action of the peptide when used as a therapeutic agent. The impurities can be unreacted starting materials, by-products of the reaction, products of side reactions, or racemization products.

Solution phase synthesis has generally been viewed as more feasible than solid phase synthesis for the large scale manufacture of eptifibatide. However, solubility issues, generation of racemization impurities and the formation of complex reaction mixtures present challenges for large scale solution phase synthesis. Complex reaction mixtures, for example, make purification of the product more difficult. Ways exist to overcome these problems, such as the use of persilylated amino acids and phase transfer reagents, as described, for example, in U.S. Pat. No. 4,954,616, and extensive chromatographic purification such as multiple preparative column chromatographies, as described in the known literature, are expensive and difficult to operate on an industrial scale.

None of the available literature teaches about the purity and impurity profile for the crude eptifibatide. In solution phase peptide synthesis repeated purification such as preparative chromatography is required to remove the impurities at crude stage; this involves consumption of large volumes of organic solvent as eluent, leads to a low yield of the final eptifibatide, which in turn result to an increase in the manufacturing cost. Thus, improvements in the synthesis such as lowering the inbuilt process impurities, leading to a robust process with minimal racemization from the initial stages of synthesis are needed.

Accordingly, there remains a need for an alternative processes to prepare eptifibatide to overcome the aforementioned difficulties, in a convenient and cost efficient manner and on a commercial scale.

The present invention provides alternate processes for the preparation of eptifibatide substantially free of racemization impurities using improved process modifications to minimize the racemization during the synthesis, as well as purification techniques that includes the use of either single preparative chromatography purification process with acetic acid as eluent or a simple flash chromatography as a substitute to expensive multiple preparative chromatography. The process of the present invention can be practiced on an industrial scale and also can be carried out without sacrifice of overall yield and purity of the product.

SUMMARY OF THE INVENTION

The invention relates processes for preparing eptifibatide. In particular, the invention encompasses (2+5), (4+3) and (3+4) solution phase peptide coupling processes for eptifibatide, and to processes for purifying eptifibatide.

In accordance with one embodiment, the present invention provides a process for the preparation of eptifibatide of Formula I:

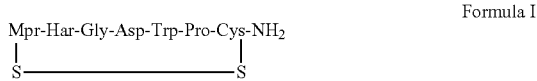

Formula I comprising:
a) coupling a 1-2 peptide fragment of formula Mpr($P_1$)—Har($P_2$)—OH with a 3-7 peptide fragment of formula Gly-Asp(O—$P_3$)-Trp($P_4$)—Pro-Cys($P_5$)—$NH_2$ in presence of a coupling agent to obtain a protected linear peptide of formula Mpr($P_1$)—Har($P_2$)-Gly-Asp(O—$P_3$)-Trp($P_4$)—Pro-Cys($P_5$)—$NH_2$,
b) deprotection of the Mpr($P_1$)—Har($P_2$)-Gly-Asp(O—$P_3$)-Trp($P_4$)—Pro-Cys($P_5$)—$NH_2$ to obtain a linear peptide of formula Mpr-Har-Gly-Asp-Trp-Pro-Cys-$NH_2$,
c) cyclizing the two sulphur atoms of the Mpr-Har-Gly-Asp-Trp-Pro-Cys-$NH_2$ to obtain eptifibatide.
wherein
Mpr is mercaptopropionic acid; Har is homoarginyl; Gly is glycyl; Asp is aspartyl; Trp is tryptophanyl; Pro is prolyl; Cys-$NH_2$ is cysteinamide;
one of $P_1$ and $P_5$ is hydrogen or a sulphur protecting group;
one of $P_2$ and $P_4$ is hydrogen or an amino protecting group; and
$P_3$ is hydrogen or a carboxyl protecting group.

In accordance with a second embodiment, the present invention provides a process for the preparation of eptifibatide of Formula I, comprising:
a) coupling Cys($P_5$)—$NH_2$ and Trp($P_4$)—Pro-OH to obtain a 5-7 peptide fragment of formula Trp($P_4$)—Pro-Cys($P_5$)—$NH_2$,
b) coupling the 5-7 peptide fragment of formula Trp($P_4$)—Pro-Cys($P_5$)—$NH_2$ and Asp(O—$P_3$)—OH to obtain a 4-7 peptide fragment of formula Asp(O—$P_3$)-Trp($P_4$)—Pro-Cys($P_5$)—$NH_2$,
c) coupling the 4-7 peptide fragment of formula Asp(O—$P_3$)-Trp($P_4$)—Pro-Cys($P_5$)—$NH_2$ and Gly-OH to obtain a 3-7 peptide fragment of formula Gly-Asp(O—$P_3$)-Trp($P_4$)—Pro-Cys($P_5$)—$NH_2$,
d) coupling the 3-7 peptide fragment of formula Gly-Asp(O—$P_3$)-Trp($P_4$)—Pro-Cys($P_5$)—$NH_2$ and a 1-2 peptide fragment of formula Mpr($P_1$)—Har($P_2$)—OH to obtain protected linear peptide of formula Mpr($P_1$)—Har($P_2$)-Gly-Asp(O—$P_3$)-Trp($P_4$)—Pro-Cys($P_5$)—$NH_2$,
e) deprotection of the Mpr($P_1$)—Har($P_2$)-Gly-Asp(O—$P_3$)-Trp($P_4$)—Pro-Cys($P_5$)—$NH_2$ to obtain linear peptide of formula Mpr-Har-Gly-Asp-Trp-Pro-Cys-$NH_2$,
f) cyclizing the two sulphur atoms of the Mpr-Har-Gly-Asp-Trp-Pro-Cys-$NH_2$ to obtain eptifibatide.

Mpr is mercaptopropionic acid; Har is homoarginyl; Gly is glycyl; Asp is aspartyl; Trp is tryptophanyl; Pro is prolyl; Cys-$NH_2$ is cysteinamide;
one of $P_1$ and $P_5$ is hydrogen or a sulphur protecting group;
one of $P_2$ and $P_4$ is hydrogen or an amino protecting group; and
$P_3$ is hydrogen or a carboxyl protecting group.

In accordance with a third embodiment, the present invention provides a 3-7 peptide fragment of formula

wherein Gly, Asp, Trp, Pro, Cys-$NH_2$, $P_3$, $P_4$ and $P_5$ are defined as above.

In accordance with a fourth embodiment, the present invention provides a 3-7 peptide fragment of formula

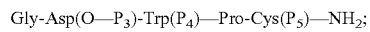

wherein Gly, Asp, Trp, Pro, Cys-$NH_2$ are defined as above; $P_3$ is tert-butyl, $P_4$ is Hydrogen and $P_5$ is Trityl group.

In accordance with a fifth embodiment, the present invention provides a process for the preparation of eptifibatide of Formula I, comprising:
a) coupling a 1-4 peptide fragment of formula Mpr($P_1$)—Har($P_2$)-Gly-Asp(O—$P_3$) with a 5-7 peptide fragment of formula Trp($P_4$)—Pro-Cys($P_5$)—$NH_2$ in presence of a coupling agent to obtain protected linear peptide of formula Mpr($P_1$)—Har($P_2$)-Gly-Asp(O—$P_3$)-Trp($P_4$)—Pro-Cys($P_5$)—$NH_2$,
b) deprotection of the Mpr($P_1$)-Har($P_2$)-Gly-Asp(O—$P_3$)-Trp($P_4$)—Pro-Cys($P_5$)—$NH_2$ to obtain linear peptide of formula Mpr-Har-Gly-Asp-Trp-Pro-Cys-$NH_2$,
c) cyclizing the two sulphur atoms of the Mpr-Har-Gly-Asp-Trp-Pro-Cys-$NH_2$ to obtain eptifibatide.
wherein Mpr is mercaptopropionic acid; Har is homoarginyl; Gly is glycyl; Asp is aspartyl; Trp is tryptophanyl; Pro is prolyl; Cys-$NH_2$ is cysteinamide;
one of $P_1$ and $P_5$ is hydrogen or a sulphur protecting group;
one of $P_2$ and $P_4$ is hydrogen or an amino protecting group; and
$P_3$ is hydrogen or a carboxyl protecting group.

In accordance with a sixth embodiment, the present invention provides a process for the preparation of eptifibatide of Formula I, comprising:
a) coupling a 1-2 peptide fragment of formula Mpr($P_1$)-Har-OH and Gly-OH to obtain a 1-3 peptide fragment of formula Mpr($P_1$)-Har($P_2$)-Gly-OH,
b) coupling the 1-3 peptide fragment of formula Mpr($P_1$)—Har($P_2$)-Gly-OH and Asp(O—$P_3$)—OH to obtain a 1-4 peptide fragment of formula Mpr($P_1$)—Har($P_2$)-Gly-Asp(O—$P_3$)—OH,
c) coupling Cys($P_5$)—$NH_2$ and a 5-6 peptide fragment of formula Trp($P_4$)—Pro-OH to obtain a 5-7 peptide fragment of formula Trp($P_4$)—Pro-Cys($P_5$)—$NH_2$,
d) coupling the 1-4 peptide fragment of formula Mpr($P_1$)-Har($P_2$)-Gly-Asp(O—$P_3$)—OH and the 5-7 peptide fragment of formula Trp($P_4$)—Pro-Cys($P_5$)—$NH_2$ to obtain protected linear peptide of formula Mpr($P_1$)—Har($P_2$)-Gly-Asp(O—$P_3$)-Trp($P_4$)—Pro-Cys($P_5$)—$NH_2$,
e) deprotection of the Mpr($P_1$)-Har($P_2$)-Gly-Asp(O—$P_3$)-TrP($P_4$)-Pro-Cys($P_5$)—$NH_2$ to obtain linear peptide of formula Mpr-Har-Gly-Asp-Trp-Pro-Cys-$NH_2$, f) cyclizing the two sulphur atoms of the Mpr-Har-Gly-Asp-Trp-Pro-Cys-NH$_2$ to obtain eptifibatide.

Mpr is mercaptopropionic acid; Har is homoarginyl; Gly is glycyl; Asp is aspartyl; Trp is tryptophanyl; Pro is prolyl; Cys-NH$_2$ is cysteinamide;

one of P$_1$ and P$_5$ is hydrogen or a sulphur protecting group; one of P$_2$ and P$_4$ is hydrogen or an amino protecting group; and P$_3$ is hydrogen or a carboxyl protecting group.

In accordance with a seventh embodiment, the present invention provides 1-4 peptide fragment of formula

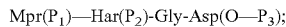

Mpr(P$_1$)—Har(P$_2$)-Gly-Asp(O—P$_3$);

wherein Mpr; Har; Gly and Asp are defined as above; P$_1$ is hydrogen or a sulphur protecting group; P$_2$ is hydrogen or an amino protecting group; and P$_3$ is hydrogen or a carboxyl protecting group.

In accordance with an eighth embodiment, the present invention provides 1-4 peptide fragment of formula

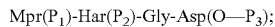

Mpr(P$_1$)-Har(P$_2$)-Gly-Asp(O—P$_3$);

wherein Mpr; Har; Gly and Asp are defined as above; P$_1$ is Trityl group, P$_2$ is hydrogen; and P$_3$ is tert-butyl group.

In accordance with a ninth embodiment, the present invention provides a process for the preparation of eptifibatide of Formula I, comprising:

a) coupling a 1-3 fragment of formula Mpr(P$_1$)—Har-Gly-OH with a 4-7 peptide fragment of formula H-Asp(O—P$_3$)-Trp-Pro-Cys(P$_5$)—NH$_2$ in presence of a coupling agent to obtain Mpr(P$_1$)—Har-Gly-Asp(O—P$_3$)-Trp-Pro-Cys(P$_5$)—NH$_2$, b) deprotection of the Mpr(P$_1$)—Har-Gly-Asp(O—P$_3$)-Trp-Pro-Cys(P$_5$)—NH$_2$ to obtain linear peptide of formula Mpr-Har-Gly-Asp-Trp-Pro-Cys-NH$_2$, c) cyclizing the two sulfur atoms from the Mpr-Har-Gly-Asp-Trp-Pro-Cys-NH$_2$ to obtain crude eptifibatide, wherein Mpr, Har, Gly, Asp, Trp, Pro, and Cys-NH$_2$ are defined as above and P$_3$ is hydrogen or a carboxyl protecting group and P$_1$ and P$_5$ is hydrogen or a sulphur protecting group.

In accordance with a tenth embodiment, the present invention provides a process for the preparation of eptifibatide of Formula I, comprising:

a) coupling of Mpr(P$_1$)—Har-OH and H-Gly-OMe to obtain 1-3 peptide fragment of formula Mpr(P$_1$)—Har-Gly-OH, b) coupling the fragment Cys(P$_5$)—NH$_2$ with a fragment Boc-Trp-Pro-OH to obtain 5-7 peptide fragment of formula H-Trp-Pro-Cys(P$_5$)—NH$_2$, c) coupling the 5-7 peptide fragment H-Trp-Pro-Cys(P$_5$)—NH$_2$ with a fragment Fmoc-Asp(O—P$_3$)—OH to obtain 4-7 peptide fragment of formula Fmoc-Asp(O—P$_3$)-Trp-Pro-Cys (P$_5$)—NH$_2$, d) treating the 4-7 peptide fragment Fmoc-Asp(O—P$_3$)-Trp-Pro-Cys(P$_5$)—NH$_2$ with a base to obtain H-Asp(O—P$_3$)-Trp-Pro-Cys(P$_5$)—NH$_2$, g) coupling the 1-3 peptide fragment of formula Mpr(P$_1$)—Har-Gly-OH and the 4-7 peptide fragment of formula H-Asp(O—P$_3$)-Trp-Pro-Cys(P$_5$)—NH$_2$ to obtain protected linear peptide of formula Mpr(P$_1$)—Har-Gly-Asp(O—P$_3$)-Trp-Pro-Cys(P$_5$)—NH$_2$, h) deprotection of the Mpr(P$_1$)—Har-Gly-Asp(O—P$_3$)-Trp-Pro-Cys(P$_5$)—NH$_2$ to obtain linear peptide of formula Mpr-Har-Gly-Asp-Trp-Pro-Cys-NH$_2$, i) cyclizing the two sulphur atoms of the Mpr-Har-Gly-Asp-Trp-Pro-Cys-NH$_2$ to obtain eptifibatide.

In accordance with an eleventh embodiment, the present invention provides H-Asp(O—P$_3$)-Trp-Pro-Cys(P$_5$)—NH$_2$ contains less than about 0.1% of one or more of impurities by HPLC: D-Cys, D-Trp, D-Pro and D-Asp isomer;

wherein P$_3$ is hydrogen or a carboxyl protecting group and P$_5$ is hydrogen or a sulphur protecting group.

In accordance with a twelfth embodiment, the present invention provides Mpr(P$_1$)—Har-Gly-OH contains less than about 0.1% of D-Har isomer by HPLC; wherein P$_1$ is hydrogen or a sulphur protecting group.

In accordance with a thirteenth embodiment, the present invention provides a process for purification of eptifibatide, comprising subjecting the crude eptifibatide to a flash chromatography system using suitable eluent selected from an alcohol, a nitrile solvent, water and an acid and mixture thereof, to obtain the pure eptifibatide.

In accordance with a fourteenth embodiment, the present invention provides eptifibatide having purity greater than about 99.5% by HPLC.

In accordance with a fifteenth embodiment, the present invention provides eptifibatide substantially free of one or more of impurities by HPLC: D-Cys, D-Har, D-Asp, D-Trp and D-Pro.

In accordance with a sixteenth embodiment, the present invention provides a pharmaceutical composition comprising eptifibatide or a salt thereof prepared by the processes of the present invention.

DETAILED DESCRIPTION OF THE INVENTION

The present invention relates to processes for preparing eptifibatide. In particular, the invention encompasses (2+5), (4+3) and (3+4) solution phase peptide coupling processes for eptifibatide, which avoids multiple preparative column purifications, thereby increasing the yield and decreasing the manufacturing cost.

As used herein, the term "carboxyl protecting group" refers to a moiety that can be selectively attached to and removed from a carboxyl group to prevent it from participating in undesired chemical reactions, without unacceptably adverse affects on desired reactions. Examples of carboxyl protecting groups include esters, such as methyl, ethyl, t-butyl, (un)substituted benzyl, cyclohexyl, 2-phenylisopropyl, 2-adamantyl and silyl esters, among others. Other carboxyl protecting groups are well known in the art and are described in detail in Protecting Groups in Organic Synthesis, Theodora W. Greene and Peter G. M. Wuts, 3rd Edition, 1999, published by John Wiley and Sons, Inc.

As used herein, the term "amino protecting group" refers to a moiety that can be selectively attached to and removed from a nitrogen atom to prevent it from participating in undesired chemical reactions, without unacceptably adverse affects on desired reactions. Examples of amino protecting groups include carbamates, such as Boc, Cbz, Fmoc, alloc, methyl and ethyl carbamates, among others; cyclic imide derivatives, such as phthalimide; amides, such as formyl, (un)substituted acetyl, and benzoyl; and trialkyl silyl groups, such as t-butyldimethylsilyl and triisopropylsilyl; toluene sulfonyl, Pmc (2,2,5,7,8-pentamethyl chroman-6-sulfonyl), Pbf (2,2,4,6,7-pentamethyl dihydrobenzofuran-5-sulfonyl), Mtr (4-methoxy-2,3,6-trimethylbenzenesulfonyl). Other amino protecting groups are well known in the art and are described in detail in Protecting Groups in Organic Synthesis, Theodora W. Greene and Peter G. M. Wuts, 3rd Edition, 1999, published by John Wiley and Son, Inc.

As used herein, the term "sulphur protecting group" refers to a moiety that can be selectively attached to and removed from a sulphur atom to prevent it from participating in undesired chemical reactions, without unacceptably adverse affects on desired reactions. Examples of sulphur protecting groups include Acm (acetamidomethyl), Trt (Trityl), t-butyl, p-methoxybenzyl, and benzyl, among others.

As used herein, the term "coupling," and all variations thereof, refers to the formation of an amide bond, by any means, between the moieties being joined.

As used herein, the term "HOBT" refers to 1-Hydroxy benzotriazole.

As used herein, the term "HOAT" refers to 1-Hydroxy-7-azabenzotriazole.

As used herein, the term "EDC" refers to 1-Ethyl-3-[3-dimethylaminopropyl]carbodiimide.

As used herein, the term "DCC" refers to dicyclohexyl carbodiimide.

As used herein, the term "CDI" refers to 1,1'-carbonyl diimidazole.

As used herein, the term "Oxyma" refers to ethyl 2-cyano-2-(hydroxyimino)acetate.

All amino acid residues referred to herein are natural amino acids that have the L-configuration.

Eptifibatide can be represented using amino acid designations as follows (SEQ ID NO:1):

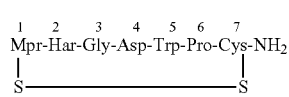

Formula I

For the ease of description, the amino acid residues can be numbered from (1) through (7). Residue (1) is mercaptopropionic acid (Mpr); (2) is homoarginyl (Har); (3) is glycyl (Gly); (4) is aspartyl (Asp); (5) is tryptophanyl (Trp); (6) is prolyl (Pro); (7) cysteinamide (Cys-NH$_2$).

In the peptide synthesis, solution phase synthesis has generally been viewed as more viable than solid phase synthesis for the large scale manufacture of eptifibatide. However, solubility issues and generation of racemization impurities are challenges for the large scale solution phase synthesis. Ways exist to overcome these problems by using purification techniques such as multiple preparative column chromatography, salt exchange, as described in the prior literature, are expensive and difficult to operate on an industrial scale. The inventors of the present invention have surprisingly been found that to overcome the aforementioned difficulties by way of minimizing the content of racemization impurities at early stages of the synthesis and also avoiding further racemization up to the crude stage of the synthesis by adopting various process modifications such as selection of coupling agents, reaction temperature, solvent purification techniques, single chromatography purification such as either preparative purification with acetic acid or a simple flash chromatography.

In one embodiment, the present invention provides a process for the preparation of eptifibatide, comprising:
a) coupling a 1-2 peptide fragment of formula Mpr(P$_1$)—Har(P$_2$)—OH with a 3-7 peptide fragment of formula Gly-Asp(O—P$_3$)-Trp(P$_4$)—Pro-Cys(P$_5$)—NH$_2$ in an organic solvent to obtain a protected linear peptide of formula Mpr(P$_1$)—Har(P$_2$)-Gly-Asp(O—P$_3$)-TrP(F$_4$)-Pro-Cys(P$_5$)—NH$_2$,
b) deprotection of the Mpr(P$_1$)—Har(P$_2$)-Gly-Asp(O—P$_3$)-Trp(P$_4$)—Pro-Cys(P$_5$)—NH$_2$ to obtain a linear peptide of formula Mpr-Har-Gly-Asp-Trp-Pro-Cys-NH$_2$,
c) cyclizing the two sulphur atoms of the Mpr-Har-Gly-Asp-Trp-Pro-Cys-NH$_2$ to obtain eptifibatide.
wherein
Mpr is mercaptopropionic acid; Her is homoarginyl; Gly is glycyl; Asp is aspartyl; Trp is tryptophanyl; Pro is prolyl; Cys-NH$_2$ is cysteinamide; one of P$_1$ and P$_5$ is hydrogen or a sulphur protecting group; one of P$_2$ and P$_4$ is hydrogen or an amino protecting group; and P$_3$ is hydrogen or a carboxyl protecting group.

Preferably, the sulphur protecting group can be selected from the group consisting of Acm (acetamidomethyl), Trt (Trityl), t-butyl, p-methoxybenzyl, and benzyl, among others; the amino protecting group can be selected from the group consisting of Boc (t-butyloxycarbonyl), Fmoc (Fluorenylmethoxy carbonyl), toluene sulfonyl, Pmc (2,2,5,7,8-pentamenthyl chroman-6-sulfonyl), Pbf (2,2,4,6,7-pentamethyl dihydrobenzofuran-5-sulfonyl), Mtr (4-methoxy-2,3,6-trimethylbenzenesulfonyl), among others; and the carboxyl protecting group can be selected from the group consisting of methyl, ethyl, t-butyl, benzyl, cyclohexyl, 2-phenylisopropyl, 2-adamantyl and silyl esters, among others.

In another embodiment, the 1-2 peptide fragment of formula Mpr(P$_1$)—Har(P$_2$)—OH, wherein the P$_1$ is trityl (Trt) and P$_2$ is hydrogen, can be prepared containing amino acids Mpr (1) and Har (2) by coupling in presence of a suitable coupling agent, a base and an organic solvent as shown in the sequence A of scheme 01. The suitable coupling agent include, but is not limited to HOBT, HOAT, DCC, EDC, CDI, Oxyma and the like and mixtures thereof. The base is selected from an organic base such as triethyl amine, diisopropyl ethyl amine, and the like or an inorganic base such as hydroxides, carbonates, bicarbonates of alkali metals; preferably the base is selected from triethyl amine or diisopropyl ethyl amine. The organic solvent includes, but is not limited to halogenated hydrocarbons such as methylene chloride, ethylene chloride, chloroform and the like; dimethyl formamide, N-methyl pyrrolidone, dimethyl sulfoxide and the like; and mixtures thereof; preferably methylene chloride.

In another embodiment, the resultant 1-2 peptide fragment of formula Mpr(Trt)-Har-OH may be purified to reduce the corresponding D-isomers. The purification may be carried by dissolving Mpr(Trt)-Har-OH in an organic solvent at pH of about 4 to 8 with a base and then slurring in water at acidic pH with an acid. The organic solvent includes but are not limited to C1-4 alcohols such as methanol, ethanol, isopropanol, n-propanol, n-butanol and the like; halogenated hydrocarbons such as methylene chloride, ethylene chloride, chloroform and the like and mixtures thereof; preferably the organic solvent is mixture of methanol and methylene chloride. The base is selected from an organic base such as triethyl amine, diisopropyl ethyl amine, and the like or an inorganic base such as hydroxides, carbonates, bicarbonates of alkali metals; preferably the base is sodium hydroxide, potassium hydroxide, sodium carbonate or potassium carbonate.

In another embodiment, the present invention provides a 1-2 peptide fragment of formula Mpr(Trt)-Har-OH contain less than 0.1% of D-Har impurity by HPLC.

In a further embodiment, the 3-7 peptide fragment of formula Gly-Asp(O—P$_3$)-Trp(P$_4$)—Pro-Cys(P$_5$)—NH$_2$ can be prepared containing amino acids Gly (3), Asp (4), Trp (5), Pro (6) and Cys-NH$_2$ (7), a one by one convergent coupling of each of the amino acid as shown in the sequence B of scheme 01.

Sequence B of scheme 01 shows the preparation of the 3-7 peptide fragment by coupling a 4-7 peptide fragment of formula Asp($P_3$)-Trp($P_4$)-Pro-Cys($P_5$)—$NH_2$ (SEQ ID NO:5) and Gly-OH, wherein the $P_3$ is tertiary butyl (tBu), $P_4$ is hydrogen and the $P_5$ is trityl group (Trt).

The 4-7 peptide fragment of formula Asp(O-tBu)-Trp-Pro-Cys(Trt)-$NH_2$ can be prepared by coupling Cys(Trt)-$NH_2$ and Trp-Pro-OH to obtain a 5-7 peptide fragment of formula Trp-Pro-Cys(Trt)-$NH_2$, which may be further coupled with Asp(O-tBu)-OH.

The coupling of Cys(Trt)-$NH_2$ and Trp-Pro-OH may be carried out in presence of a coupling agent and a base in an organic solvent. The coupling agent may be selected from the group consisting of HOBT, HOAT, DCC, EDC, CDI, Oxyma and the like and mixtures thereof. The base is selected from an organic base such as triethyl amine, diisopropyl ethyl amine, and the like or an inorganic base such as hydroxides, carbonates, bicarbonates of alkali metals; preferably the base is selected from triethyl amine or diisopropyl ethyl amine. The organic solvent includes, but are not limited to halogenated hydrocarbons such as methylene chloride, ethylene chloride, chloroform and the like; dimethyl formamide, N-methyl pyrrolidone, dimethyl sulfoxide and the like; and mixtures thereof; preferably methylene chloride.

The coupling of a 5-7 peptide fragment of formula Trp-Pro-Cys(Trt)-$NH_2$ and Asp(O-tBu)-OH may be carried out in presence of a coupling agent and a base in an organic solvent. The coupling agent may be selected from the group consisting of HOBT, HOAT, DCC, EDC, CDI, Oxyma and the like and mixtures thereof. The base is selected from an organic base such as triethyl amine, diisopropyl ethyl amine, piperidine and the like or an inorganic base such as hydroxides, carbonates, bicarbonates of alkali metals; preferably the base is selected from triethyl amine, piperidine or diisopropyl ethyl amine. The organic solvent includes, but are not limited to halogenated hydrocarbons such as methylene chloride, ethylene chloride, chloroform and the like; dimethyl formamide, N-methyl pyrrolidone, dimethyl sulfoxide and the like; and mixtures thereof; preferably methylene chloride.

The resultant 4-7 peptide fragment of formula Asp(O-tBu)-Trp-Pro-Cys(Trt)-$NH_2$ may be purified to reduce the corresponding D-isomers. The purification may be carried out by, the 4-7 peptide fragment of formula Asp(O-tBu)-Trp-Pro-Cys(Trt)-$NH_2$ may be treated with a base and/or a solvent crystallization in presence of an organic solvent $S_1$. The base can be selected from the group consisting of piperidine, diethyl amine, diisopropyl amine, N-methyl morpholine (NMM), 1,8-Diazabicyclo[5.4.0]undec-7-ene (DBU) and the like and mixtures thereof; preferably the base is peperidine.

The organic solvent $S_1$ include, but are not limited to $C_{1-4}$ alcohols, halogenated hydrocarbons, aromatic hydrocarbons, esters, ethers, ketones, linear and cyclic hydrocarbons, nitriles, and mixtures thereof. Preferably the organic solvent $S_1$ is selected from the group consisting of methanol, methylene chloride, toluene, ethyl acetate, isopropyl ether; more preferably methylene chloride or isopropyl ether.

The 4-7 peptide fragment of formula Asp(O-tBu)-Trp-Pro-Cys(Trt)-$NH_2$ may be coupled with Gly-OH to obtain a 3-7 peptide fragment of formula Gly-Asp(O-tBu)-Trp-Pro-Cys(Trt)-$NH_2$. The 3-7 peptide fragment formation may be carried out in presence of a coupling agent and an organic solvent optionally in presence of a base. The coupling agent may be selected from the group consisting of HOBT, HOAT, DCC, EDC, CDI, Oxyma and the like and mixtures thereof. The base is selected from an organic base such as triethyl amine, diisopropyl ethyl amine, piperidine, diethyl amine, diisopropyl amine, N-methyl morpholine (NMM), 1,8-Diazabicyclo[5.4.0]undec-7-ene (DBU) and the like and mixtures thereof or an inorganic base such as hydroxides, carbonates, bicarbonates of alkali metals; preferably triethyl amine, diisopropyl ethyl amine or piperidine. The organic solvent includes, but are not limited to halogenated hydrocarbons such as methylene chloride, ethylene chloride, chloroform and the like; dimethyl formamide, N-methyl pyrrolidone, dimethyl sulfoxide and the like; and mixtures thereof; preferably methylene chloride.

The resultant 3-7 peptide fragment of formula Gly-Asp(O-tBu)-Trp-Pro-Cys(Trt)-$NH_2$ can be purified to reduce the corresponding D-isomers. The purification may be carried out with a solvent crystallization in presence of an organic solvent $S_1$ as in described above.

The 3-7 peptide fragment of formula Gly-Asp(O-tBu)-Trp-Pro-Cys(Trt)-$NH_2$ recovered using the process of the present invention may have a chemical purity of greater than about 97% and contain less than about 0.1% by HPLC of one or more of D-Asp, D-Trp, D-Pro and D-Cys isomer wherein the corresponding amino acid unit in the L-configuration in Gly-Asp(O-tBu)-Trp-Pro-Cys(Trt)-$NH_2$ is the D-isomer formed in the synthetic sequence.

In an embodiment, the present invention provides a 3-7 peptide fragment of formula Gly-Asp($P_3$)-Trp($P_4$)-Pro-Cys ($P_5$)—$NH_2$ (SEQ ID NO:6) wherein $P_3$ is hydrogen or a carboxyl protecting group; $P_4$ is hydrogen or an amino protecting group; and $P_5$ is hydrogen or a sulphur protecting group; preferably $P_3$ is tertiary butyl, $P_4$ is hydrogen and $P_5$ is Trityl group. The 3-7 peptide fragment of formula Gly-Asp($P_3$)-Trp($P_4$)-Pro-Cys($P_5$)—$NH_2$ (SEQ ID NO:6) can be purified to remove racemization impurities Gly-Asp($P_3$)-Trp ($P_4$)-Pro-Cys($P_5$)(D)-$NH_2$ (SEQ ID NO:7), Gly-Asp($P_3$)(D)-Trp($P_4$)-Pro-Cys($P_5$)—$NH_2$ (SEQ ID NO:8), Gly-Asp($P_3$)-Trp($P_4$)(D)-Pro-Cys($P_5$)—$NH_2$ (SEQ ID NO:9), and Gly-Asp($P_3$)-Trp($P_4$)-Pro(D)-Cys($P_5$)—$NH_2$ (SEQ ID NO:10) to less than about 0.1% by HPLC.

Step a) of foregoing process may be carried out by coupling a 1-2 peptide fragment of formula Mpr($P_1$)-Har ($P_2$)—OH with a 3-7 peptide fragment of formula Gly-Asp ($P_3$)-Trp($P_4$)-Pro-Cys($P_5$)—$NH_2$ (SEQ ID NO:6) in presence of a coupling agent in an organic solvent to obtain a protected linear peptide of formula Mpr($P_1$)-Har($P_2$)-Gly-Asp($P_3$)-Trp($P_4$)-Pro-Cys($P_5$)—$NH_2$ (SEQ ID NO:3); wherein the $P_1$ is Trityl, $P_2$ is hydrogen, $P_3$ is tertiary butyl, $P_4$ is hydrogen and $P_5$ is trityl group. The coupling agent include but are not limited to HOBT, HOAT, DCC, EDC, CDI, Oxyma and the like and mixtures thereof. The organic solvent includes, but is not limited to halogenated hydrocarbons such as methylene chloride, ethylene chloride, chloroform and the like; dimethyl formamide, N-methyl pyrrolidone, dimethyl sulfoxide and the like; and mixtures thereof; preferably methylene chloride or dimethyl formamide.

The reaction temperature should be sufficient to effect the coupling reaction. Typically the reaction temperature may be from about −30° C. to about +25° C.; preferably at about −20° C. to 10° C., more preferably at about −10° C. to 0° C.

The fragment Mpr(Trt)-Har-Gly-Asp(O-tBu)-Trp-Pro-Cys(Trt)-$NH_2$ may be optionally purified. The purification may be carried out in presence of an organic solvent. The organic solvent include, but are not limited to $C_{1-4}$ alcohols such as methanol, ethanol, n-propanol, isopropanol, n-butanol, isobutanol and the like and mixtures thereof; esters such as methyl acetate, ethyl acetate, isopropyl acetate and the like and mixtures thereof; amides such as dimethyl formamide, N-methyl pyrrolidine and the like and mixtures thereof; dimethyl sulfoxide; ketones such as acetone, methyl ethyl ketone, methyl isobutyl ketone and the like and mixtures thereof; halogenated hydrocarbons such as methylene chloride, ethylene chloride, chloroform and the like and mixtures thereof. Preferably the organic solvent is selected from methylene chloride, chloroform, toluene, acetone, ethyl acetate and cyclohexane, more preferably in a mixture of methylene chloride and ethyl acetate.

The resultant protected linear peptide of formula Mpr (Trt)-Har-Gly-Asp(O-tBu)-Trp-Pro-Cys(Trt)-$NH_2$ may be deprotected to obtain a linear peptide of formula Mpr-Har-Gly-Asp-Trp-Pro-Cys-$NH_2$. The deprotection may be carried out in presence of a suitable deprotecting agent and optionally in a solvent. The suitable deprotecting agent may be selected from the group consisting of an acid such as trifluoroacetic acid, hydrobromic acid, acetic acid, hydrogen fluoride and the like optionally in presence of trimethyl silyl bromide (TMSBr), trifluoromethansulfoacid (TFMSA), triisopropyl silane. The solvent include, but are not limited to halogenated hydrocarbons such as methylene chloride, ethylene chloride, chloroform and the like; water and mixtures thereof. Preferably the deprotection is carried out in presence of trifluoroacetic acid and triisopropyl silane in methylene chloride and water.

The cyclization step of Mpr-Har-Gly-Asp-Trp-Pro-Cys-$NH_2$ may be carried out with a suitable cyclizing agent and in a suitable solvent system in presence of a base at a temperature of about −25° C. to about 35° C. The base can be inorganic base or organic base, for example sodium or potassium hydroxide, sodium or potassium carbonate, ammonium hydroxide, ammonium carbonate, diethyl amine, diisopropyl amine, diisopropyl ethyl amine, triethyl amine, piperidine, N-methyl morpholine and the like and mixtures thereof; preferably ammonium hydroxide. The cyclizing agent may be selected from the group consisting of atmospheric air, oxygen gas, hydrogen peroxide; preferably oxygen gas or atmospheric air, and a suitable solvent system selected from nitriles such as acetonitrile, propionitrile and the like; $C_{1-4}$ alcohol such as methanol, ethanol, isopropanol and the like; ethers such as tetrahydrofuran, dioxane and the like; water; and mixtures thereof; preferably mixture of acetonitrile and water.

In another embodiment, the present invention provides a process for the preparation of eptifibatide, comprising:

a) coupling a 1-4 peptide fragment of formula Mpr($P_1$)-Har($P_2$)-Gly-Asp($P_3$) (SEQ ID NO:2) with a 5-7 peptide fragment of formula Trp($P_4$)-Pro-Cys($P_5$)—$NH_2$ in an organic solvent to obtain a protected linear peptide of formula Mpr($P_1$)-Har($P_2$)-Gly-Asp($P_3$)-Trp($P_4$)-Pro-Cys($P_5$)—$NH_2$ (SEQ ID NO:3), b) deprotection of the Mpr($P_1$)-Har($P_2$)-Gly-Asp($P_3$)-Trp($P_4$)-Pro-Cys($P_5$)—$NH_2$ (SEQ ID NO:3) to obtain a linear peptide of formula Mpr-Har-Gly-Asp-Trp-Pro-Cys-$NH_2$ (SEQ ID NO:4), c) cyclizing the two sulphur atoms of the Mpr-Har-Gly-Asp-Trp-Pro-Cys-$NH_2$ (SEQ ID NO:4) to obtain eptifibatide (SEQ ID NO:1), wherein one of $P_1$ and $P_5$ is hydrogen or a sulphur protecting group; one of $P_2$ and $P_4$ is hydrogen or an amino protecting group; and $P_3$ is hydrogen or a carboxyl protecting group.

wherein
one of $P_1$ and $P_5$ is hydrogen or a sulphur protecting group;
one of $P_2$ and $P_4$ is hydrogen or an amino protecting group; and
$P_3$ is hydrogen or a carboxyl protecting group.

Preferably, the sulphur protecting group can be selected from the group consisting of Acm (acetamidomethyl), Trt (Trityl), t-butyl, p-methoxybenzyl, and benzyl, among others; the amino protecting group can be selected from the group consisting of Boc (t-butyloxycarbonyl), Fmoc (Fluorenylmethoxy carbonyl), toluene sulfonyl, Pmc (2,2,5,7,8-pentamenthyl chroman-6-sulfonyl), Pbf (2,2,4,6,7-pentamethyl dihydrobenzofuran-5-sulfonyl), Mtr (4-methoxy-2,3,6-trimethylbenzenesulfonyl), among others; and the carboxyl protecting group can be selected from the group consisting of methyl, ethyl, t-butyl, benzyl, cyclohexyl, 2-phenylisopropyl, 2-adamantyl and silyl esters, among others.

The 1-4 peptide fragment of formula Mpr($P_1$)—Har($P_2$)-Gly-Asp(O—$P_3$); wherein $P_1$ Trityl group, $P_2$ is hydrogen and $P_3$ is tertiary butyl, can be prepared containing amino acids Mpr (1), Har (2), Gly (3), and Asp(4), by a one by one convergent coupling of each of the amino acid as shown in the sequence C of scheme 02. The 1-4 peptide coupling may be carried in presence of a suitable coupling agent, a base and an organic solvent. The suitable coupling agent include, but is not limited to HOBT, HOAT, DCC, EDC, CDI, Oxyma and the like and mixtures thereof. The base is selected from an organic base such as triethyl amine, diisopropyl ethyl amine, piperidine, diethyl amine, diisopropyl amine, N-methyl morpholine (NMM), 1,8-Diazabicyclo [5.4.0]undec-7-ene (DBU) and the like and mixtures thereof or an inorganic base such as hydroxides, carbonates, bicarbonates of alkali metals; preferably triethyl amine, diisopropyl ethyl amine or piperidine. The organic solvent includes, but is not limited to halogenated hydrocarbons such as methylene chloride, ethylene chloride, chloroform and the like; dimethyl formamide, N-methyl pyrrolidone, dimethyl sulfoxide and the like; and mixtures thereof; preferably methylene chloride or dimethyl formamide.

The 1-4 peptide fragment of formula Mpr(Trt)-Har-Gly-Asp(O-tBu) recovered using the process of the present invention may have a chemical purity of greater than about 95% and contain less than about 0.1% by HPLC of D-Har isomer.

In an embodiment, the present invention provides a 1-4 peptide fragment of formula Mpr($P_1$)—Har($P_2$)-Gly-Asp (O—$P_3$); wherein the $P_1$ is hydrogen or a sulphur protecting group, $P_2$ is hydrogen or an amino protecting group; and $P_3$ is hydrogen or a carboxyl protecting group; preferably $P_1$ is Trityl group, $P_2$ is hydrogen and $P_3$ is tertiary butyl.

The 5-7 peptide fragment of formula Trp($P_4$)—Pro-Cys ($P_5$)—$NH_2$; wherein the $P_4$ is hydrogen and the $P_5$ is trityl group, may be prepared containing amino acids Trp (5), Pro (6), and Cys-$NH_2$ (7), a one by one convergent coupling of each of the amino acid as process described above.

The coupling step of a 1-4 peptide fragment of formula Mpr(Trt)-Har-Gly-Asp(O-tBu) with a 5-7 peptide fragment of formula Trp-Pro-Cys(Trt)-$NH_2$ obtained by the processes described above may be carried out in presence of a coupling agent and an organic solvent to obtain a protected linear peptide of formula Mpr(Trt)-Har-Gly-Asp(O-tBu)-Trp-Pro-Cys(Trt)-$NH_2$. The coupling agent include but are not limited to HOBT, HOAT, DCC, EDC, CDI, Oxyma and the like and mixtures thereof. The organic solvent includes, but is not limited to halogenated hydrocarbons such as methylene chloride, ethylene chloride, chloroform and the like; dimethyl formamide, N-methyl pyrrolidone, dimethyl sulfoxide and the like; and mixtures thereof; preferably methylene chloride or dimethyl formamide.

The reaction temperature should be sufficient to effect the coupling reaction. Typically the reaction temperature may be from about −30° C. to about +25° C.; preferably at about −20° C. to 10° C., more preferably at about −5° C. to 0° C.

The protected linear peptide of formula Mpr(Trt)-Har-Gly-Asp(O-tBu)-Trp-Pro-Cys(Trt)-$NH_2$ thus obtained is converted into eptifibatide by deprotection of the protecting groups and then cyclization of the resultant linear peptide by the processes as described above.

In another embodiment, the present invention provides a process for the preparation of eptifibatide, comprising:
a) coupling a 1-3 fragment of formula Mpr($P_1$)—Har-Gly-OH with a 4-7 peptide fragment of formula H-Asp(O—$P_3$)-Trp-Pro-Cys($P_5$)—$NH_2$ in presence of a coupling agent to obtain Mpr($P_1$)—Har-Gly-Asp(O—$P_3$)-Trp-Pro-Cys($P_5$)—$NH_2$,
b) deprotection of the Mpr($P_1$)—Har-Gly-Asp(O—$P_3$)-Trp-Pro-Cys($P_5$)—$NH_2$ to obtain linear peptide of formula Mpr-Har-Gly-Asp-Trp-Pro-Cys-$NH_2$,
c) cyclizing the two sulfur atoms from the Mpr-Har-Gly-Asp-Trp-Pro-Cys-$NH_2$ to obtain crude eptifibatide,
wherein Mpr, Har, Gly, Asp, Trp, Pro, and Cys-$NH_2$ are defined as above and $P_3$ is hydrogen or a carboxyl protecting group and $P_1$ and $P_5$ is hydrogen or a sulphur protecting group.

The 4-7 fragment H-Asp(O—$P_3$)-Trp-Pro-Cys($P_5$)—$NH_2$, wherein $P_3$ is tertiary butyl and $P_5$ is trityl, can be prepared containing amino acids Asp (4), Trp (5), Pro (6), and Cys-$NH_2$ (7), by a one by one convergent coupling of each of the amino acid as shown in the scheme 03.

The coupling of Cys(Trt)-$NH_2$ and a fragment Boc-Trp-Pro-OH may be carried out in presence of a suitable coupling agent and a base in an organic solvent. The suitable coupling agent may be selected from the group consisting of HOBT, HOAT, DCC, EDC, CDI, Oxyma and the like and mixtures thereof. The base is selected from an organic base such as triethyl amine, diisopropyl ethyl amine, piperidine, diethyl amine, diisopropyl amine, N-methyl morpholine (NMM), 1,8-Diazabicyclo[5.4.0]undec-7-ene (DBU) and the like and mixtures thereof or an inorganic base such as hydroxides, carbonates, bicarbonates of alkali metals, preferably triethylamine or diisopropyl ethylamine. The organic solvent includes, but are not limited to halogenated hydrocarbons such as methylene chloride, ethylene chloride, chloroform and the like; dimethyl formamide, N-methyl pyrrolidone, dimethyl sulfoxide and the like; and mixtures thereof; preferably the organic solvent is methylene chloride.

The coupling of fragment H-Trp-Pro-Cys(Trt)-$NH_2$ and a fragment Fmoc-Asp(O-tBu)-OH may be carried out in presence of a coupling agent and a base in an organic solvent at a temperature of about −20° C. to about +20° C. The coupling agent may be selected from the group consisting of HOBT, HOAT, DCC, EDC, CDI and the like and mixtures thereof. The base is an organic base such as triethyl amine, diisopropyl ethyl amine, and the like; preferably diisopropyl ethyl amine. The organic solvent includes, but are not limited to halogenated hydrocarbons such as methylene chloride, ethylene chloride, chloroform and the like; dimethyl formamide, N-methyl pyrrolidone, dimethyl sulfoxide and the like; and mixtures thereof; preferably the organic solvent is methylene chloride.

Further, the resultant compound Fmoc-Asp(O-tBu)-Trp-Pro-Cys(Trt)-$NH_2$ can be treated with an inorganic base or amine base to remove the Fmoc protecting group at a temperature of about 5° C. to about 40° C. for about 6 to about 12 hours, preferably the reaction is carried out at a temperature of about 25° C. to about 35° C. for 8 hours. The amine base used for deprotection include, but are not limited diethyl amine, diisopropyl amine, piperidine, N-methyl morpholine (NMM), 1,8-Diazabicyclo[5.4.0]undec-7-ene (DBU) and the like and mixtures thereof; preferably the amine base is piperidine.

Then, the fragment H-Asp(O-tBu)-Trp-Pro-Cys(Trt)-$NH_2$ may be optionally purified. The purification may be carried out by solvent crystallization in presence of an organic solvent. The organic solvent include, but are not limited to $C_{1-4}$ alcohols such as methanol, ethanol, n-propanol, isopropanol, n-butanol and the like and mixtures thereof; halogenated hydrocarbons such as methylene chloride, ethylene chloride, chloroform and the like and mixtures thereof; aromatic hydrocarbons such as toluene, xylene and the like and mixtures thereof; esters such as methyl acetate, ethyl acetate, isopropyl acetate and the like and mixtures thereof; ethers such as diethyl ether, diisopropyl ether, methyl tertiary butyl ether, tetrahydrofuran, 1,4-dioxane; and the like and mixtures thereof; ketones such as acetone, methyl ethyl ketone, methyl isobutyl ketone and the like and mixtures thereof; linear and cyclic hydrocarbons such as hexane, heptane, cyclohexane and the like and mixtures thereof; nitriles such as acetonitrile, propionitrile and the like, and mixtures thereof. Preferably the organic solvent is selected from methylene chloride, toluene, ethyl acetate, acetone, and cyclohexane, more preferably a mixture of toluene and methylene chloride.

The fragment H-Asp(O-tBu)-Trp-Pro-Cys(Trt)-$NH_2$ recovered using the process of the present invention may have a chemical purity of greater than about 97% and contain less than about 0.1% by HPLC of one or more of D-Cys, D-Trp, D-Pro and D-Asp isomer.

In an embodiment, the present invention provides fragment H-Asp(O-tBu)-Trp-Pro-Cys(Trt)-$NH_2$ contains less than about 0.1% by HPLC of one or more of D-Cys, D-Trp, D-Pro and D-Asp isomer.

The 1-3 fragment Mpr($P_1$)—Har-Gly-OH, wherein $P_1$ is trityl, can be prepared containing amino acids Mpr (1), Har (2), and Gly (3), by a one by one convergent coupling of each of the amino acid as shown in the scheme 03.

The coupling of fragment Mpr(Trt)-Har-OH and a fragment H-Gly-OMe may be carried out in presence of a coupling agent, a metal salt and a base in an organic solvent. The coupling agent may be selected from the group consisting of HOST, HOAT, DCC, EDC, CDI, Oxyma and the like and mixtures thereof. The metal salt may be selected from copper or zinc halides, preferably copper (II) chloride. The base is an organic base such as triethyl amine, diisopropyl ethyl amine, and the like; preferably triethylamine. The organic solvent includes, but are not limited to halogenated hydrocarbons such as methylene chloride, ethylene chloride, chloroform and the like; dimethyl formamide, N-methyl pyrrolidone, dimethyl sulfoxide and the like; and mixtures thereof; preferably the organic solvent is dimethyl formamide.

Further, the resultant compound Mpr(Trt)-Har-Gly-OMe may be treated with an aqueous base solution to remove the ester protecting group at a temperature of about 10° C. to about 40° C. in an organic solvent.

Then, the fragment Mpr(Trt)-Har-Gly-OH may be optionally purified. The purification may be carried out by solvent crystallization or slurring in presence of an organic solvent. The organic solvent include, but are not limited to $C_{1-4}$ alcohols such as methanol, ethanol, n-propanol, isopropanol, n-butanol, isobutanol and the like and mixtures thereof; esters such as methyl acetate, ethyl acetate, isopropyl acetate and the like and mixtures thereof; amides such as dimethyl formamide, N-methyl pyrrolidine and the like and mixtures thereof; dimethyl sulfoxide; ketones such as acetone, methyl ethyl ketone, methyl isobutyl ketone and the like and mixtures thereof; halogenated hydrocarbons such as methylene chloride, ethylene chloride, chloroform and the like and mixtures thereof. Preferably the organic solvent is selected from methanol, methylene chloride, chloroform, toluene, dimethyl sulfoxide, acetone and cyclohexane, more preferably mixture of dimethyl sulfoxide and chloroform.

The fragment Mpr(Trt)-Har-Gly-OH recovered using the process of the present invention may have a chemical purity of greater than about 97% and contain less than about 0.1% of D-Har by HPLC.

In an embodiment, the present invention provides Mpr(Trt)-Har-Gly-OH contains less than about 0.1% of D-Har by HPLC.

The coupling of the fragment Mpr(Trt)-Har-Gly-OH (1-3 fragment) and H-Asp(O-tBu)-Trp-Pro-Cys(Trt)-NH$_2$ (4-7 fragment) may be carried out in presence of a coupling agent in an organic solvent at a temperature of about −25° C. to 10° C. The coupling agent may be selected from the group consisting of HOBT, MOAT, DCC, EDC, CDI, Oxyma and the like and mixtures thereof. The organic solvent includes, but are not limited to halogenated hydrocarbons such as methylene chloride, ethylene chloride, chloroform and the like; amides such as dimethyl formamide, N-methyl pyrrolidine and the like; and mixtures thereof, dimethyl sulfoxide; preferably the organic solvent is dimethyl formamide and the reaction temperature is about −15° to about −10° C.

The fragment Mpr(Trt)-Har-Gly-Asp(O-tBu)-Trp-Pro-Cys(Trt)-NH$_2$ may be optionally purified by the purification process as described above.

The protected linear peptide of formula Mpr(Trt)-Har-Gly-Asp(O-tBu)-Trp-Pro-Cys(Trt)-NH$_2$ thus obtained is converted into eptifibatide by deprotection of the protecting groups and then cyclization of the resultant linear peptide by the processes as described above.

The eptifibatide as obtained by a processes of the present invention may have a chemical purity of greater than about 90% by HPLC and contain less than about 0.2% by HPLC of one or more of related impurities such as D-Cys, D-Har, D-Asp, D-Trp and D-Pro isomer. The quality of the eptifibatide can be improved by purifying the eptifibatide using a preparative chromatography or a flash chromatography method.

In an embodiment, the present invention provides a process for purification of eptifibatide, comprising subjecting the crude eptifibatide to a flash chromatography system using suitable eluent.

In a further embodiment the present invention provides any form of eptifibatide or eptifibatide thus obtained by the processes of the present invention may be purified by flash chromatography method. The flash chromatography method can be performed using Reveleris flash chromatography system and an eluent comprising an alcohol, a nitrile solvent, water and an acid and mixtures thereof. The eluent is selected from the group consisting of methanol, ethanol, isopropanol, acetonitrile, propionitrile, acetic acid, trifluoro acetic acid, water and mixtures thereof. The flash chromatography column may be selected from any column known in the art suitable for flash chromatography, for example, preferably C18 silica column with about 5 to about 50 µm particles. Flow rate of the eluent may be selected from any flow rate that is eptifibatide and its isomers are separable; typically flow rate may be selected from about 10 ml to 100 ml per minute. Conditions for the flash chromatography are known to the person skilled in the art.

After collecting fractions containing eptifibatide from the chromatography, the pure eptifibatide can be isolated from the resultant mass by conventional techniques such as crystallization or lyophilization methods known in the art. This may allow for a high purity level of the resulting eptifibatide from the crude compound, e.g., a chemical purity of at least about 99% preferably at least about 99.5% and more preferably at least about 99.8% and contain less than about 0.15% by HPLC of one or more of D-Cys, D-Har, D-Asp, D-Trp and D-Pro isomer.

In an embodiment, the present invention provides a process for purification of eptifibatide, comprising subjecting the crude eptifibatide to a preparative high performance liquid chromatography (preparative HPLC) using suitable eluent.

In another embodiment, the present invention provides any form of eptifibatide or eptifibatide thus obtained may be purified by preparative high performance liquid chromatography method (preparative HPLC). The preparative HPLC can be performed using preparative HPLC system and an eluent comprising an alcohol, a nitrile solvent, water and an acid and mixtures thereof. The eluent is selected from the group consisting of methanol, ethanol, isopropanol, acetonitrile, propionitrile, acetic acid, water and mixtures thereof. The preparative chromatography column may be selected from any column known in the art suitable for preparative chromatography, for example, preferably from about 250× 30 mm to about 500×50 mm of Inertsil prep-ODS with about 5 to about 50 µm particles. Flow rate of the eluent may be selected from about 10 ml to 100 ml per minute. Conditions for the preparative HPLC are known to the person skilled in the art.

The present invention provides eptifibatide, obtained by the processes described herein, having a purity of at least about 98% as measured by HPLC, preferably at least about 99% as measured by HPLC; more preferably at least about 99.5% as measured by HPLC and substantially free of one or more of D-Cys, D-Har, D-Asp, D-Trp and D-Pro isomer, wherein the term "substantially free" refers to eptifibatide having less than about 0.15% of D-Cys, D-Har, D-Asp, D-Trp or D-Pro, as measured by HPLC, more preferably less than about 0.05% of D-Cys, D-Har, D-Asp, D-Trp or D-Pro.

The present invention provides eptifibatide, obtained by the above processes, as analyzed using high performance liquid chromatography ("HPLC") with the conditions described below:

| | |
|---|---|
| Column | Symmetry shield RP 8, (150 × 4.6) mm, 3.5 mm |
| Flow rate | 1.0 mL/minute |
| Detection | UV at 220 nm |
| Run time | 100 minutes |
| Column temp | 45° C. |
| Mobile phase A | 0.03M KH$_2$PO$_4$ in water, adjust pH to 3. 0 with orthophosphoric acid |
| Mobile phase B | Acetonitrile |

Gradient:

| Time | Mobile phase A % | Mobile phase A % |
|---|---|---|
| 0 | 95 | 5 |
| 60 | 85 | 15 |
| 90 | 40 | 60 |
| 95 | 95 | 5 |
| 100 | 95 | 5 |

In another embodiment, the present invention is directed to a pharmaceutical composition containing at least the substantially pure eptifibatide or a salt thereof disclosed herein and at least one pharmaceutically acceptable excipient. Such pharmaceutical composition may be administered to a mammalian patient in any dosage form, e.g., liquid, powder, elixir, injectable solution, etc.
The present invention provides processes for the preparation of eptifibatide is prepared according to Scheme 01, Scheme 02 and Scheme 03:
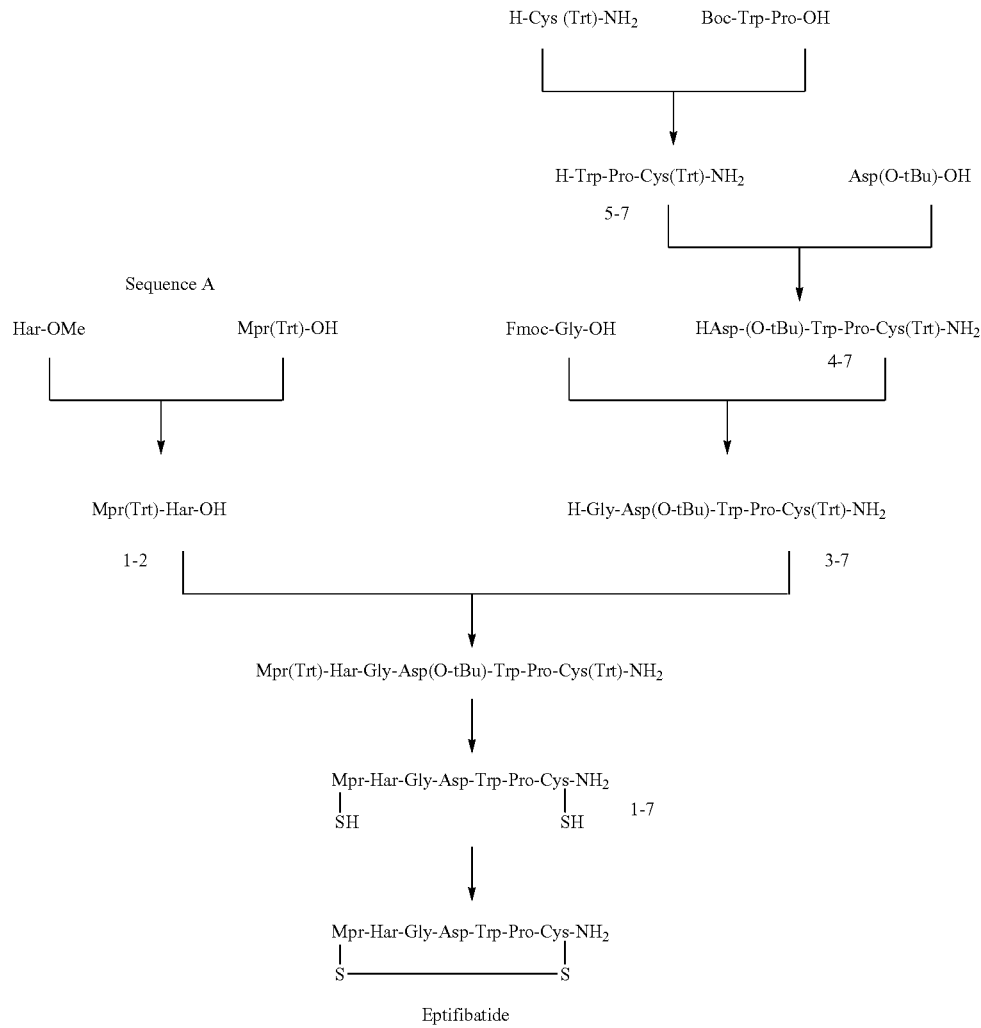
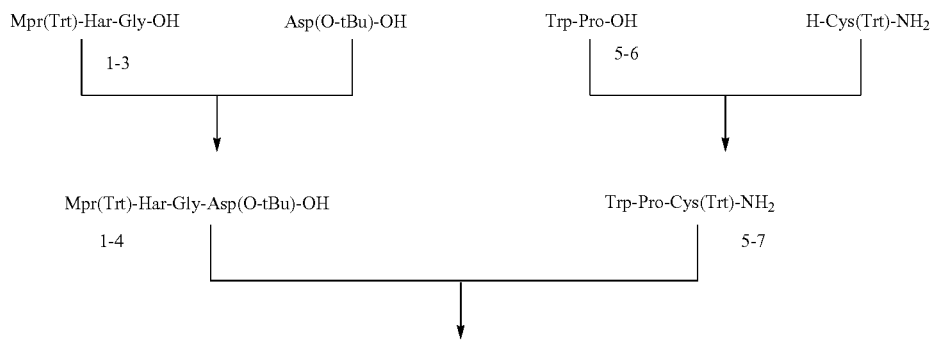

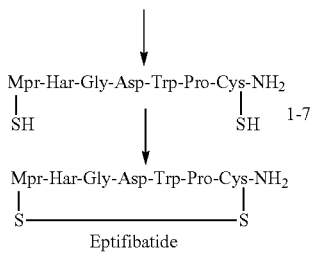

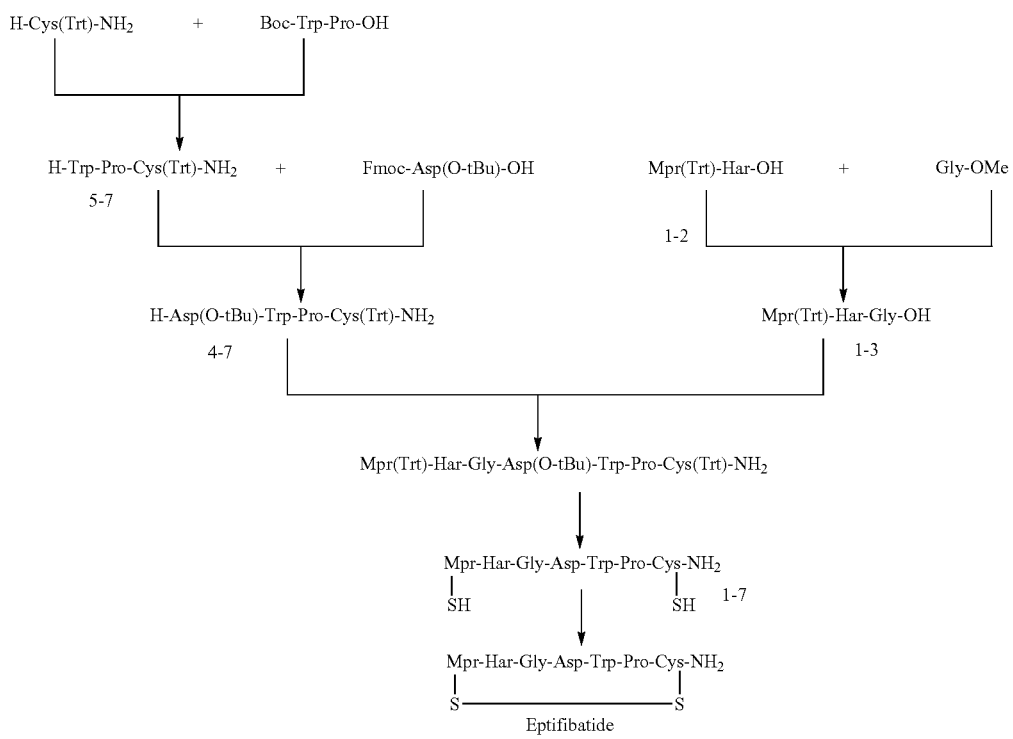

EXAMPLES

The following examples are provided to enable one skilled in the art to practice the invention and are merely illustrative of the invention. The examples should not be read as limiting the scope of the invention as defined in the claims.

Example 1: Preparation of Mpr(Trt)-Har-OH a) Preparation of Mpr(Trt)-Har-OMe To a stirred solution of L-homoarginine hydrochloride (100 g) in methanol (500 ml) was added thionyl chloride (50 ml), over a period of 30-45 min. The temperature of the reaction mass was raised to reflux and maintained at reflux for 5-9 hours. After completion of reaction, the reaction mass was concentrated under vacuum to obtain residue. Charged methylene chloride (400 ml) and triethylamine (50 ml) to the resultant residue and cooled to about 0° C. to about −5° C. Charged a mixture of Mpr(Trt)-OH (106.9 gm), triethylamine (25 ml), EDAC.HCl (94.1 gm) in methylene chloride (450 ml) about 0° C. to about −5° C. Stirred for 4 hours at the same temperature and after heated to about 25° C. to about 30° C. Added DM water (1000 nil) and stirred for 3-5 hours. The precipitated solid was filtered and the wet material was slurred in DM water. The filtered solid was dried, under vacuum for 2-4 hours and again slurred in hexane and filtered to afford a white solid material (150 gm) HPLC Purity: 95%; Chiral purity: 99.9%.

b) Preparation of Mpr(Trt)-Har-OH

To a stirred solution of Mpr(Trt)-Har-OMe (100 gm) in a mixture of methanol (800 ml) and 1,4-dioxane (300 ml) at 0-10° C., was charged a solution of 1N aqueous NaOH (650 ml). Stirred for 4 hours at same temperature and then, the reaction mixture was cooled to about 0° C.-10° C. and acidified with addition of 1N aqueous HCl (620 ml). The precipitate formed was filtered and washed with water. The wet material was co-evaporated with acetonitrile and then isolated from IPE to afford a white solid material as crude (90 gm)

HPLC Purity: 96%; Chiral purity: 99.8% c) Purification of Mpr(Trt)-Har-OH

The crude material (90 g) was added to a mixture of methanol (1800 ml) and dichloromethane (90 ml) at 25-35° C. The pH of the mixture was adjusted to 6.0-7.0 with 2% solution of NaOH in methanol. The temperature of the reaction mass was raised to 50-55° C. and maintained for 10-20 min. The reaction mass was allowed to cool to 20-25° C. and stirred at the same temperature for 4-6 hours. The white colored precipitate was filtered and the wet cake washed with methanol. The solid material dried under vacuum, at 25-35° C., for 30-45 min and then in a vacuum oven at 50-55° C. for 2 h.

The semi-dried material (75 gm) was slurred in DM water (900 ml) at 25-35° C. and the pH of the slurry adjusted to <1 with 1N HCl (ca 250 ml). The thick precipitate was slurred for another 60-75 min, and filtered. The wet cake washed with water. The wet cake was dried under vacuum for 15-30 min and slurred, successively, in DM water (700 ml) and isopropyl ether (700 ml). The white colored powder was dried at 50-55° C., under vacuum, till the moisture content was below 1%. The desired product was obtained in a yield of 60-70% with the content of D-Har enantiomer less than 0.15%.

Example 2: Preparation of H-Cys(Trt)-$NH_2$ a) Preparation of Boc-Cys(Trt)-$NH_2$ To a stirred solution of Boc-Cys(Trt)-OH (100 gm) in methylene chloride (1000 ml) at −10 to 0° C., was charged sequentially, a solution of DCC (57.9 g) in methylene chloride (125 ml) and HOBT (34.8 gm) in dimethyl formamide (70 ml). Stirred the solution for 30 minutes at the same temperature and then charged ammonia solution (120 ml). After completion of the reaction the resultant precipitate was filtered and the filtrate was taken and washed with 10% sodium bicarbonate solution. The separated organic layer was concentrated and crystallized the product Boc-Cys(Trt)-$NH_2$ from ethyl acetate and hexane (Yield: 100 g, HPLC Purity 98%, Chiral purity: 99.9% and D-Cys: 0.1%).

b) Preparation of H-Cys(Trt)-$NH_2$

To the Boc-Cys(Trt)-$NH_2$ (100 gm), added formic acid (600 ml) at temperature of about 10° C. to about 20° C. Heated the solution to about 20° C. to about 35° C. and stirred for 30 minutes at the same temperature. Added an additional quantity of formic acid (200 ml) and stirred for two hours. Cooled the reaction mass to about 0° C. to about −10° C. and charged methylene chloride (1000 ml), DM water (100 ml) and adjusted pH to 7.5-9.0 with 8N aqueous Sodium hydroxide solution. Heated the solution to about 25° C. to about 35° C. and separated the organic layer and extracted the aqueous layer with methylene chloride (250 ml) and separated the aqueous and organic layer. Combined the organic layer and washed with DM water and concentrated the organic layer under reduced pressure to obtain the residue. The residue was crystallized from hexane (100 ml) to obtain the H-Cys(Trt)-$NH_2$ as white solid material.

Yield: 85.0 g, HPLC Purity: 97%, Chiral purity: 99.9%, D-Cys: 0.1%.

Example 3: Preparation of H-Trp-Pro-Cys(Trt)-$NH_2$ a) Preparation of Boc-Trp-Pro-Cys(Trt)-$NH_2$ To a stirred solution of Boc-Trp-Pro-OH (100 gm) and triethyl amine (24 ml) in methylene chloride (1100 ml) at 0° C. to 10° C., was charged EDAC (71.6 gm) and HOBT (37.4 gm). Stirred for 30 to 60 minutes at same temperature and then added a solution of H-Cys(Trt)-$NH_2$ (75.7 gm; obtained from example-2) in methylene chloride (1000 ml). After completion of the reaction, the reaction mass was washed with an aqueous sodium bicarbonate solution and the separated organic layer was concentrated under reduced pressure and isolated from IPE to afford a white solid material (150 gm) HPLC Purity: 95.2%; Chiral purity: 99.5%, D-Cys isomer: 0.1% b) Preparation of H-Trp-Pro-Cys(Trt)-$NH_2$

A solution of Boc-Trp-Pro-Cys(Trt)-$NH_2$ (100 gm) in formic acid (800 ml) was stirred at about 25° C. to about 35° C. for 2-3 hours. After completion of the reaction the reaction mass was diluted with ethyl acetate and washed with DM water. The separated organic layer was cooled to 0° C.-10° C. and adjusted pH to 9-11 with 8N aqueous sodium hydroxide solution. Heated to 25° C.-35° C. and separated the layers. Taken organic layer and washed with DM water and then concentrated under reduced pressure. The product was isolated from IPE as white solid material (70 gm) HPLC Purity: 95%; Chiral purity: 99.5%, D-Cys isomer: 0.1%.

Example 4: Preparation of H-Asp(O-tBu)-Trp-Pro-Cys(Trt)-$NH_2$

To a stirred solution of Fmoc-Asp(O-tBu)-OH (70.2 gm) and diisopropyl ethyl amine (10 ml) in methylene chloride (1500 ml) at −10° C. to 0° C., was charged EDAC.HCl (44.5 gm) and HOBT (20.9 gm). The stirring was continued for 30-45 minutes and then H-Trp-Pro-Cys(Trt)-$NH_2$ (100 gm; obtained from example 3) was charged. Stirred for 4 hours at same temperature and washed the reaction mass with aqueous sodium bicarbonate solution and then brine solution. To the separated organic layer piperidine (60 ml) was added at 25° C. to 35° C. and stirred for 2 hours. The reaction mass was washed with DM water and then brine solution. The separated organic layer was concentrated under reduced pressure and isolated from IPE as a white solid material and then slurred in DM water and filtered.

HPLC purity: 95.2%; D-Cys isomer: 0.6%, D-Asp isomer: 0.5%

The wet compound was dissolved in methylene chloride (1000 ml) and washed with water. The organic layer was concentrated and the resultant residue was crystallized from toluene to afford a white solid material (80 gm)

HPLC Purity: 96%; Chiral purity: 99.5%, D-Cys isomer: 0.1%, D-Asp isomer: 0.1%

Example 5: Preparation of H-Gly-Asp (O-tBu)-Trp-Pro-Cys(Trt)-$NH_2$

To a stirred solution of Fmoc-Gly-OH (19 gm) in methylene chloride (500 ml), at −5° C. to 0° C. was charged EDAC.HCl (18.4 gm) and HOBT (10.4 gm). Stirred for 30-40 minutes and charged H-Asp(O-tBu)-Trp-Pro-Cys (Trt)-$NH_2$ (50 gm; obtained from example-4). Stirred for 4 hours at same temperature and after completion of the reaction added DM water to the reaction mass and the layers was separated. To the separated organic layer piperidine (30 ml) was charged at 25° C.-35° C. and stirred for 5-8 hours at same temperature. The reaction mixture was washed with DM water and then brine solution. The separated organic layer was concentrated under reduced pressure and isolated from IPE as a white solid material. The solid wet material was slurred in DM water and filtered followed by dried to afford a title compound (38 gm)

HPLC Purity: 95%; Chiral purity: 98.5%; D-Asp isomer: 0.1%

Example 6: Preparation of Mpr(Trt)-Har-Gly-Asp (O-tBu)-Trp-Pro-Cys(Trt)-NH$_2$ (2+5) Coupling Method To a stirred solution of Mpr(Trt)-Har-OH (12 gm; obtained from example-1) in dimethyl formamide (850 ml) at −10° C. to 0° C., was charged EDAC.HCl (8.8 gm) and HOBT (6.2 gm). Stirred for 30-60 minutes and then charged H-Gly-Asp (O-tBu)-Trp-Pro-Cys(Trt)-NH$_2$ (20 gm; obtained from example-5). Stirred for 4 to 6 hours at same temperature and after completion of the reaction the reaction mixture was added slowly into 10% brine solution. The precipitated solid material was filtered and the wet compound was dissolved in methylene chloride and the organic layer was washed with water. The separated organic layer was concentrated, under reduced pressure and isolated from ethyl acetate as white solid material (22 gm)

HPLC Purity: 95%, Chiral purity: 99.5%

Example 7: Preparation of Eptifibatide (2+5) Coupling Method

To a stirred solution of triisopropyl silane (14 ml), water (10 ml) and trifluoroacetic acid (160 ml) at −10° C. to −5° C. was charged a solution of Mpr (Trt)-Har-Gly-Asp(O-tBu)-Trp-Pro-Cys(Trt)-NH$_2$ (20 gm; obtained from example-6) in methylene chloride (160 ml). The reaction mass was stirred at −5° C. to −10° C. for about 5-10 hours. To the reaction mixture ethyl acetate (100 ml) and isopropyl ether (600 ml) were added and the slurry was stirred for 15-30 minutes at 0° C. to 5° C. The precipitate was filtered and washed with IPE to afford a linear peptide. The resultant crude linear peptide was charged in to a stirred solution of water (150 ml) and acetonitrile (150 ml) at 25° C. to 35° C. The pH of the reaction mass was adjusted to 7.5-9.5 with 2% ammonium hydroxide solution. Oxygen gas was purged in to the reaction mass. The progress of the reaction mass was monitored by HPLC. After the completion of reaction the pH was adjusted pH to 5.0-5.5 with 1% acetic acid. The reaction mass was concentrated and then lyophilized to fine powder (6 gm)

HPLC Purity: 90%; Chiral purity: 99%

Example 8: Preparation of Mpr(Trt)-Har-Gly-OH

To a stirred solution of Mpr(Trt)-Har-OH (50 gm; obtained from example-1) and triethylamine (10 ml) in dimethyl formamide (250 nil) at 20° C.-35° C., was charged cupric chloride (7 gm). The reaction mixture was stirred for 15-30 minutes and then cooled to 0° C.-5° C. Charged HOBT (26 gm) and EDAC.HCl (28 gm) and stirred for 10-20 minutes at same temperature. Charged H-Gly-OMe HCl (13.5 gm) and triethyl amine (8 ml) and stirred the reaction mixture at 0° C.-5° C. for 4-6 hours. The insoluble material was filtered and taken filtrate, added methylene chloride and washed with water. The organic layer was washed with aqueous EDTA solution and brine solution. Concentrated the organic layer under vacuum and the residue obtained was dissolved in a mixture of methylene chloride (150 ml) and methanol (400 ml). Charged 1N aqueous NaOH solution (350 ml) at 0° C.-5° C. and maintained at the same temperature. After completion of reaction pH was adjusted to acidic with addition of 2N aqueous HCl. Filtered the precipitate and washed with mixture of water and methanol and dried under vacuum. The crude material was purified in a mixture of DMSO and chloroform to afford a white solid material (40 gm)

HPLC Purity: 96%; Chiral purity: 99.75%.

Example 9: Preparation of Mpr(Trt)-Har-Gly-Asp(O-tBu)-OH

To a stirred solution of Mpr(Trt)-Har-Gly-OH (5.7 gm; obtained from example-8) in dimethyl formamide (30 ml) at −15° C. to −10° C. was charged HOBT (2.66 gm) and EDAC.HCl (3.78 gm). Added H-Asp(O-tBu)-OMe (2 gm) in dimethyl formamide (10 ml) and stirred at −15° C. to −10° C. for 4-6 hours. The reaction mixture was allowed to warm to 25° C. to 30° C. and methylene chloride (100 ml) was added and washed with water and then brine solution. The separated organic layer was concentrated under reduced pressure and the residue obtained was added to a mixture of 1,4-dioxane (20 ml) and methanol (50 m) at 25° C.-35° C. The solution was cooled to 0° C.-5° C. and charged 2N aqueous sodium hydroxide solution (8 ml). Stirred at 0° C.-5° C. for 2 to 3 hours and adjusted pH to acidic with addition of 2N aqueous NCl, The slurry formed was stirred for another 20-30 min, at 0° C.-5° C. Filtered the precipitate and washed with water and dried to afford a white powder (2.5 gm)

HPLC Purity: 95%, Chiral purity: 96%.

Example 10

Preparation of Mpr(Trt)-Har-Gly-Asp(O-tBu)-Trp-Pro-Cys(Trt)-NH$_2$ (4+3) Coupling Method A solution of Mpr(Trt)-Har-Gly-Asp(O-tBu)-OH (2.5 gm; obtained from example-9) in methylene chloride (25 ml) was cooled to −5° C. to 0° C. and then charged HOBT (0.91 gm) and EDAC.HCl (1.28 gm). Stirred for 45-60 minutes at same temperature and added H-Trp-Pro-Cys(Trt)-NH$_2$ (2.0 gm; obtained from example-3) and stirred for 4 to 6 hours at same temperature. After completion of the reaction the reaction mixture was washed with water and then organic layer was concentrated under reduced pressure. The residue obtained was dissolved in DMF and the solution was added to brine solution. The precipitate formed was slurred for another 30-45 minutes and filtered and then dried to afford a white solid material (2.5 gm) HPLC Purity: 90%, Chiral purity: 95%.

Example 11: Preparation of Eptifibatide (4+3) Coupling Method

To a stirred solution of triisopropyl silane (1.4 ml), water (2 ml) and trifluoroacetic acid (16 ml) at −10° C. to −5° C. was charged a solution of Mpr (Trt)-Har-Gly-Asp(O-tBu)-Trp-Pro-Cys(Trt)-NH$_2$ (2.0 gm; obtained from example-10) in methylene chloride (16 ml). The reaction mass was stirred at −5° C. to −10° C. for about 5-10 hours, To the reaction mixture ethyl acetate (10 ml) and isopropyl ether (60 ml) were added and the slurry was stirred for 15-30 minutes at 0° C. to 5° C. The precipitate was filtered and washed with IPE to afford a linear peptide. The resultant crude linear peptide was charged in to a stirred solution of water (16 ml) and acetonitrile (16 ml) at 25° C. to 35° C. The pH of the reaction mass was adjusted to 7.5-9.5 with 2% ammonium hydroxide solution. Oxygen gas was purged in to the reaction mass. The progress of the reaction mass was monitored by HPLC. After the completion of reaction the pH was adjusted pH to 5.0-5.5 with 1% acetic acid. The reaction mass was concentrated and then lyophilized to fine powder (0.7 gm)

HPLC Purity: 90%; Chiral purity: 99%

Example 12: Preparation of H-Cys(Trt)-NH$_2$ a) Preparation of Boc-Cys(Trt)-NH$_2$ To a stirred solution of Boc-Cys(Trt)-OH (100 gm) in methylene chloride (1000 ml) at −10 to 0° C., was charged sequentially, a solution of DCC (57.9 g) in methylene chloride (125 ml) and HOST (34.8 gm) in dimethyl formamide (70 nil). Stirred the solution for 30 minutes at the same temperature and then charged ammonia solution (120 ml). After completion of the reaction the resultant precipitate was filtered and the filtrate was taken and washed with 10% sodium bicarbonate solution. The separated organic layer was concentrated and crystallized the product Boc-Cys(Trt)-NH$_2$ from ethyl acetate and hexane (Yield: 100 g, HPLC Purity 98%, Chiral purity: 99.9% and D-Cys: 0.1%).

b) Preparation of H-Cys(Trt)-NH$_2$

To the Boc-Cys(Trt)-NH$_2$ (100 gm), added formic acid (600 ml) at temperature of about 10° C. to about 20° C. Heated the solution to about 20° C. to about 35° C. and stirred for 30 minutes at the same temperature. Added an additional quantity of formic acid (200 ml) and stirred for two hours. Cooled the reaction mass to about 0° C. to about −10° C. and charged methylene chloride (1000 ml), DM water (100 ml) and adjusted pH to 7.5-9.0 with 8N aqueous Sodium hydroxide solution. Heated the solution to about 25° C. to about 35° C. and separated the organic layer and extracted the aqueous layer with methylene chloride (250 ml) and separated the aqueous and organic layer. Combined the organic layer and washed with DM water and concentrated the organic layer under reduced pressure to obtain the residue. The residue was crystallized from hexane (100 ml) to obtain the H-Cys(Trt)-NH$_2$ as white solid material.

Yield: 65.0 g, HPLC Purity: 97%, Chiral purity: 99.9%, D-Cys: 0.1%.

Example 13

Preparation of H-Cys(Trt)-NH$_2$ using a procedure analogous to that employed in Example 12, but using combination of different coupling agents and reaction temperature for 100 gms of starting material Boc-Cys(Trt)-OH, as described in the following Table I:

TABLE I

| Coupling agent | | Reaction Temperature | Chemical Purity | Chiral Purity | D-Cys |
|---|---|---|---|---|---|
| EDC (62 gm) | HOBT (30.8 gm) | 0° C. to 5° C. | 98% | 93.89% | 6.11% |
| EDC (62 gm) | HOBT (30.8 gm) | 5° C. to 10° C. | 97.8% | 88.58% | 11.42% |
| CDI (46 gm) | | 20° C. to 25° C. | 95% | 92.39% | 7.61% |

Example 14: Preparation of H-Trp-Pro-Cys(Trt)-NH$_2$ a) Preparation of Boc-Trp-Pro-Cys(Trt)-NH$_2$ To a stirred solution of Boc-Trp-Pro-OH (76 gm) and triethylamine (18.5 ml) in methylene chloride (850 ml) at about 0° C. to about −10° C., was charged EDC (54.5 gm) and HOBT (28.5 gm). Stirred for 30 minutes and charged H-Cys(Trt)-NH$_2$ (65 gm, obtained from Ex-12) in methylene chloride (750 ml) at same temperature. After completion of the reaction organic layer was subjected to washings with aqueous sodium bicarbonate, aqueous citric acid solution. The separated organic layer was concentrated under reduced pressure and the resultant residue was crystallized in isopropyl ether to obtain Boc-Trp-Pro-Cys(Trt)-NH$_2$ as a white solid material.

Yield: 115 gm, HPLC Purity: 95%, Chiral purity: 99.5%, D-Trp: 0.1%, D-Pro: 0.1%, D-Cys: 0.1%.

b) Preparation of H-Trp-Pro-Cys(Trt)-NH$_2$

To the Boc-Trp-Pro-Cys(Trt)-NH$_2$ (100 gm), added formic acid (800 ml) at temperature of about 20° C. to about 35° C. Stirred for 60 minutes at same temperature and charged ethyl acetate, DM water to the reaction mass and separated the aqueous and organic layers. Washed the organic layer with DM water and separated the layers. Taken organic layer and cooled to about 0° C. to about 10° C. and adjusted pH to 10-12 with 8N aqueous sodium hydroxide solution. Heated the solution to about 25° C. to about 35° C. and separated the organic layer. Concentrated the organic layer under reduced pressure to obtain the residue, which was crystallized from isopropyl ether to obtain H-Trp-Pro-Cys(Trt)-NH$_2$ as white solid material.

Yield: 72 gm, HPLC Purity: 95%, Chiral purity: 99.5%, D-Trp: 0.1%, D-Pro: 0.1%, D-Cys: 0.1%.

Example 15: Preparation of H-Asp(O-tBu)-Trp-Pro-Cys(Trt)-NH$_2$

To a stirred solution of Fmoc-Asp(O-tBu)-OH (49.5 gm) and diisopropyl ethyl amine (7 ml) in methylene chloride (1050 ml) at a temperature of about −10° C. to about 0° C., was charged, EDC.HCl (31.5 gm) and HOBT (14.8 gm). Stirred for 30 minutes at same temperature and charged H-Trp-Pro-Cys(Trt)-NH$_2$ (70 gm; obtained from Ex-14) and stirred for 8 hours at same temperature and after completion of the reaction, the reaction mass was washed with aqueous sodium bicarbonate solution. Separated the organic layer and charged piperidine (42 ml) at 25° C.-35° C. Stirred for 8 hours at same temperature and after completion of the reaction, washed the reaction mass with DM water and then brine solution. Separated the organic layer and concentrated under reduced pressure followed by resultant residue was crystallized from isopropyl ether to obtain the title compound as a white solid (HPLC purity: 95%, D-Cys: 0.3%). To the resultant wet material charged methylene chloride (700 ml) and washed the solution with DM water. The separated organic layer was concentrated under reduced pressure and the resultant residue was crystallized from toluene as a white solid material.

Yield: 58 gm, HPLC Purity: 96%, Chiral purity: 99.5%, D-Trp: 0.1%, D-Pro: 0.1%, D-Cys: 0.1%, D-Asp: 0.1%.

Example 16: Preparation of Mpr(Trt)-Har-Gly-OH

To a stirred solution of Mpr(Trt)-Har-OH (100 gm) and triethylamine (20 ml) in dimethyl formamide (500 ml) at 20° C.-35° C., was charged copper (II) chloride (13.4 gm). Stirred for 20 minutes at same temperature and the reaction mixture was cooled to −15° C. to −5° C. Charged HOBT (52 gm) and EDC. HCl (55.5 gm) and stirred for 20 minutes at −15° C. to −5° C. and then charged H-Gly-OMe HCl (26.6 gm) and triethyl amine (16 ml) at same temperature. Heated the solution to −5° C. and stirred at −5° C. to 0° C., 3-4 hours. After completion of the reaction, filtered the reaction mass and taken filtrate and extracted with methylene chloride (1×800 ml and 0.1×200 ml). Separated the layers and combined the organic layers and washed with water. The separated organic layer was distilled off completely under vacuum till a thick residue was obtained, To the resultant residue, charged methylene chloride (300 ml) and methanol (800 ml) at 25° C.-35° C., Added 1N aqueous sodium hydroxide solution (690 ml) and cooled to 0° C.-5° C. and stirred for 30 minutes at same temperature. After completion of reaction adjusted pH to 2.0 with 2N aqueous hydrochloric acid (600 ml). Filtered the precipitated solid and washed with water and methanol to obtain the crude product. The crude product was recrystallized from a mixture of dimethyl sulfoxide and chloroform to obtain the title compound.

Yield: 85.0 gm, HPLC Purity: 96%, Chiral purity: 99.95%, D-Har: 0.05%.

Example 17

Preparation of Mpr(Trt)-Har-Gly-OH using a procedure analogous to that employed in Example 16, but using combination of different coupling agents, reaction temperature and with or without use of copper (II) chloride for 100 gms of starting material Mpr(Trt)-Har-OH, as described in the following Table II:

TABLE II

| Coupling agent | | Copper (II) Chloride | Reaction Temperature | Chemical Purity | Chiral Purity | D-Har |
|---|---|---|---|---|---|---|
| EDC (56 gm) | HOBT (52 gm) | 13.4 gm | 0° C. to 5° C. | 96.56% | 99.75% | 0.25% |
| EDC (59 gm) | HOBT (29 gm) | Nil | −5° C. to 0° C. | 93% | 53.46% | 46.54% |
| DCC (60 gm) | HOBT (29 gm) | Nil | −5° C. to 0° C. | 91.5% | 99.43% | 0.57% |
| EDC (55 gm) | Oxyma (30 gm) | Nil | −10° C. to −5° C. | 96.75% | 99.16% | 0.84% |

Example 18: Preparation of Mpr(Trt)-Har-Gly-Asp (O-tBu)-Trp-Pro-Cys(Trt)-NH$_2$ (3+4) Coupling Method To a stirred solution of Mpr(Trt)-Har-Gly-OH (70 gm; obtained from Ex-16) and dimethyl formamide (800 ml) at −15° C. to −10° C., charged HOBT (33 gm), EDC.HCl (47 gm) and a solution of H-Asp(O-tBu)-Trp-Pro-Cys(Trt)-NH$_2$ (100 gm; obtained from Ex-15) in dimethyl formamide (400 ml). The reaction mass was stirred for 4-7 hours at the same temperature and after completion of the reaction, charged 10% aqueous sodium chloride (3000 ml) to the reaction mass. Stirred for 60 minutes at temperature of about 5° C. to 10° C. and filtered the precipitated solids. Slurred the resultant solids in water and filtered the solids and the wet material was dissolved in methylene chloride (2000 ml). Washed the resultant solution with an aqueous sodium bicarbonate and separated the layers. Taken organic layer and concentrated under reduced pressure to obtain residue. The residue was crystallized from ethyl acetate to obtain the title compound as white solid.

Yield: 150 gm, HPLC Purity: 96%, Chiral purity: 99.5%, D-Trp: 0.1%, D-Pro: 0.1%, D-Cys: 0.1%, D-Asp: 0.1% and D-Har: Not detected.

Example 19: Preparation of Mpr-Har-Gly-Asp-Trp-Pro-Cys-NH$_2$ (3+4) Coupling Method To a stirred solution of trifluoroacetic acid (800 ml), triisopropyl silane (70 ml) and water (50 ml) at −10° C. to −5° C., was charged a solution of Mpr(Trt)-Har-Gly-Asp (O-tBu)-Trp-Pro-Cys(Trt)-NH$_2$ (100 gm; obtained from Ex-18) in methylene chloride (800 ml). The reaction mass was stirred for 5-8 hours at temperature −10° C. to −5° C. After completion of the reaction, charged ethyl acetate (400 ml) and isopropyl ether (3000 ml) and stirred for 30 minutes at temperature 0° C. to 5° C. Filtered the precipitated solids and slurred the solids in n-butanol. Filtered the title product and washed with n-butanol.

Yield: 60 gm, HPLC Purity: 85%, Chiral purity: 99.5%, D-Trp: 0.1%, D-Pro: 0.1%, D-Cys: 0.1%, & D-Asp: 0.2%.

Example 20

Preparation of Eptifibatide (3+4) Coupling Method

Mpa-Har-Gly-Asp-Trp-Pro-Cys-NH$_2$ (60 gm; obtained from Ex-19) was charged in to a stirred solution of water (6 L) and acetonitrile (6 L) at 25° C.-35° C. Adjusted the pH of the solution to 8-8.5 with 2% ammonium hydroxide solution (500 ml). Passed oxygen gas in to the reaction mass for about 10 to 12 hrs under pH of about 8.5-about 8.8. Adjusted pH of the reaction mass to about 5 to about 6 with 1% acetic acid 100 ml) and concentrated the reaction solution at 30° C. to 35° C. under high vacuum till 30% of the solution remains in the reaction vessel and then lyophilized the reaction solution to obtain the title compound.

Yield: 45 gm, HPLC Purity: 90%, Chiral purity: 99.0%, D-Trp: 0.1%, D-Pro: 0.1%, D-Cys: 0.1%, D-Asp: 0.2% & D-Har: 0.3%.

Example 21: Purification of Eptifibatide Using Flash Chromatography (Acetonitrile:Water)

Crude eptifibatide (5 gm; obtained from Example 7) was purified by Revelries flash chromatography system using reverse phase C18 silica column under the following chromatography conditions:

| | |
|---|---|
| Column: | Revelries reverse phase C18 silica, particle size 40μ |
| Flow rate: | 35 ml/min |
| Detection: | By UV at 220 nm |
| Runtime: | 62 min |
| Mobile phase A: | 0.25% acetic acid in water |
| Mobile phase B: | 0.025M ammonium acetate in water:acetonitrile (1:1) |
| Gradient (T/% B): | 0/5, 5/5, 10/30, 40/30, 1/100, 6/100 |

All peak fractions were collected (approximate volume: 420 ml) and the pure fractions were concentrated until 200 ml remains in the vessel and then lyophilized to obtain pure eptifibatide acetate.

Yield: 2.8 gm, HPLC Purity: 99.5%, D-Cys: 0.05%, D-Har: 0.2%.

D-Trp, D-Pro & D-Asp: Not detected.

Example 21: Purification of Eptifibatide Using Flash Chromatography (Methanol:Water)

Crude eptifibatide (5 gm; obtained from Ex-20) was purified by Revelries flash chromatography system using reverse phase C18 silica column under the following chromatography conditions:

| | |
|---|---|
| Column: | Revelries reverse phase C18 silica, particle size 40μ |
| Flow rate: | 35 ml/min |
| Detection: | By UV at 220 nm |
| Runtime: | 59 min |
| Mobile phase A: | 0.25% acetic acid in water |
| Mobile phase B: | 0.025M ammonium acetate in water:methanol (1:1) |
| Gradient (T/% B): | 0/5, 5/5, 10/70, 33/70, 1/100, 10/100 |

All peak fractions were collected (approximate volume: 420 ml) and the pure fractions were concentrated until 200 ml remains in the vessel and then lyophilized to obtain pure eptifibatide acetate.

Yield: 2.75 gm, HPLC Purity: 99.5%, D-Cys: 0.04%, D-Har: 0.21%.

D-Trp, D-Pro & D-Asp: Not detected.

Example 22

Purification of Eptifibatide Using Preparative High Performance Liquid Chromatography Crude eptifibatide (5 gm; obtained from Ex-20) was purified by preparative HPLC using Inertsil prep-ODS column under the following chromatography conditions:

| | |
|---|---|
| Column: | Inertsil prep-ODS(250 × 50 mm); particle size 10μ |
| Flow rate: | 60 mL/minute |
| Detection: | By UV at 220 nm |
| Runtime: | 20 minutes |
| Mobile phase A: | 0.25% Acetic acid in water |
| Mobile phase B: | 0.025M Ammonium acetate in water:Acetonitrile (1:1) |
| Gradient (T/% B): | 0/5, 10/5, 15/15, 25/15, 45/50, 50/50, 50.05/100, 55/100, 55.5/5, 60.0/5.0 |

All peak fractions were collected and lyophilized to afford white colored solid material eptifibatide acetate.

Yield: 2.43 gm, HPLC purity: 99.4%, D-Cys: 0.06%, D-Har: 0.19%.

D-Trp, D-Pro & D-Asp: Not detected.

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the specification appended hereto.

We claim:

1. A process for preparation of eptifibatide of Formula I (SEQ ID NO:1):

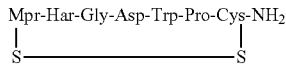

Formula I wherein Mpr is mercaptopropionic acid, Har is homoarginyl, Gly is glycyl, Asp is aspartyl, Trp is tryptophanyl, Pro is prolyl, and Cys-NH$_2$ is cysteinamide, the process comprising the steps of:
 a) coupling Cys($P_5$)—NH$_2$ and Trp($P_4$)-Pro-OH to obtain a peptide fragment of formula Trp($P_4$)-Pro-Cys($P_5$)—NH$_2$;
 b) coupling the peptide fragment of formula Trp($P_4$)-Pro-Cys($P_5$)—NH$_2$ and Asp($P_3$)—OH to obtain a peptide fragment of formula Asp($P_3$)-Trp($P_4$)-Pro-Cys($P_5$)—NH$_2$ (SEQ ID NO:5);
 c) coupling the peptide fragment of formula Asp($P_3$)-Trp($P_4$)—Pro-Cys($P_5$)—NH$_2$ (SEQ ID NO:5) and Gly-OH to obtain a peptide fragment of formula Gly-Asp($P_3$)-Trp($P_4$)-Pro-Cys($P_5$)—NH$_2$ (SEQ ID NO:6);
 d) purifying the peptide fragment of formula Gly-Asp($P_3$)-Trp($P_4$)-Pro-Cys($P_5$)—NH$_2$ (SEQ ID NO:6) produced in step c) to less than 0.1% Gly-Asp($P_3$)-Trp($P_4$)-Pro-Cys($P_5$)(D)-NH$_2$ (SEQ ID NO:7), Gly-Asp($P_3$)(D)-Trp($P_4$)-Pro-Cys($P_5$)—NH$_2$ (SEQ ID NO:8), Gly-Asp($P_3$)-Trp($P_4$)(D)-Pro-Cys($P_5$)—NH$_2$ (SEQ ID NO:9), or Gly-Asp($P_3$)-Trp($P_4$)-Pro(D)-Cys($P_5$)—NH$_2$ (SEQ ID NO:10) by HPLC;
 e) coupling the peptide fragment of formula Gly-Asp($P_3$)-Trp($P_4$)-Pro-Cys($P_5$)—NH$_2$(SEQ ID NO:6) and a 1-2 peptide fragment of formula Mpr($P_1$)-Har($P_2$)—OH to obtain protected linear peptide of formula Mpr($P_1$)-Har($P_2$)-Gly-Asp($P_3$)-Trp($P_4$)-Pro-Cys($P_5$)—NH$_2$ (SEQ NO:3);
 f) optionally purifying Mpr($P_1$)-Har($P_2$)-Gly-Asp($P_3$)-Trp($P_4$)-Pro-Cys($P_5$)—NH$_2$(SEQ NO:3);
 g) deprotection of the Mpr($P_1$)-Har($P_2$)-Gly-Asp($P_3$)-Trp($P_4$)-Pro-Cys($P_5$)—NH$_2$(SEQ NO:3) to obtain linear peptide of formula Mpr-Har-Gly-Asp-Trp-Pro-Cys-NH$_2$ (SEQ ID NO:4); and
 h) cyclizing the two sulphur atoms of the Mpr-Har-Gly-Asp-Trp-Pro-Cys-NH$_2$ (SEQ ID NO:4) to obtain eptifibatide of Formula I (SEQ ID NO:1),
 wherein each one of $P_1$ and $P_5$ is one of hydrogen and a sulphur protecting group, each one of $P_2$ and $P_4$ is one of hydrogen and an amino protecting group, and $P_3$ is one of hydrogen and a carboxyl protecting group.

2. The process of claim 1, wherein the coupling is carried out with a suitable coupling agent selected from the group consisting of HOBT, HOAT, DCC, EDC, CDI, ethyl 2-cyano-2-(hydroxyimino)acetate, and mixtures thereof.

3. The process of claim 1, wherein the step g) is carried out with a suitable deprotecting agent selected from the group consisting of trifluoroacetic acid, hydrobromic acid, acetic acid, and hydrogen fluoride; and
 wherein the step h) is carried out in the presence of atmospheric air, oxygen gas or hydrogen peroxide.

4. The process of claim 1 further comprising the step of subjecting the eptifibatide obtained from step h) to a flash chromatography system using an eluent to obtain pure eptifibatide.

5. The method of claim 4, wherein the eluent is selected from the group consisting of alcohols, nitrile solvents, water, acids, and mixtures thereof.

6. The method of claim 4, wherein the eluent is selected from the group consisting of methanol, ethanol, isopropanol, acetonitrile, propionitrile, acetic acid, trifluoro acetic acid, water, and mixtures thereof.

7. The method of claim 4, wherein the pure eptifibatide has a purity of at least 99%.

* * * * *

SEQUENCE LISTING

```
<160> NUMBER OF SEQ ID NOS: 10

<210> SEQ ID NO 1
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is mercaptopropionic acid
<220> FEATURE:
<221> NAME/KEY: MISC_FEATURE
<222> LOCATION: (1)..(7)
<223> OTHER INFORMATION: 1,7 disulfide bond
<220> FEATURE:
<221> NAME/KEY: MISC_FEATURE
<222> LOCATION: (2)..(2)
<223> OTHER INFORMATION: Xaa is homoarginyl
<220> FEATURE:
<221> NAME/KEY: MISC_FEATURE
<222> LOCATION: (7)..(7)
<223> OTHER INFORMATION: Cys-NH2 is cysteinamide

<400> SEQUENCE: 1

Xaa Xaa Gly Asp Trp Pro Cys
1               5

<210> SEQ ID NO 2
<211> LENGTH: 4
<212> TYPE: PRT
<213> ORGANISM: Artificial Sequence
<220> FEATURE:
<223> OTHER INFORMATION: Synthetic Construct
```

```
<220> FEATURE:
<221> NAME/KEY: MISC_FEATURE
<222> LOCATION: (1)..(1)
<223> OTHER INFORMATION: Xaa is mercaptopropionic acid, P1 is a
      hydrogen or a sulphur protecting group
<220> FEATURE:
<221> NAME/KEY: MISC_FEATURE
<222> LOCATION: (2)..(2)
<223> OTHER INFORMATION: Xaa is homoarginyl, P2 is a hydrogen or an
      amino protecting group

<400> SEQUENCE: 2

Xaa Xaa Gly Asp
1

<210> SEQ ID NO 3
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is mercaptopropionic acid, P1 is a
      hydrogen or a sulphur protecting group
<220> FEATURE:
<221> NAME/KEY: MISC_FEATURE
<222> LOCATION: (2)..(2)
<223> OTHER INFORMATION: Xaa is homoarginyl, P2 is a hydrogen or an
      amino protecting group
<220> FEATURE:
<221> NAME/KEY: MISC_FEATURE
<222> LOCATION: (4)..(4)
<223> OTHER INFORMATION: P3 is a hydrogen or a carboxyl protecting group
<220> FEATURE:
<221> NAME/KEY: MISC_FEATURE
<222> LOCATION: (5)..(5)
<223> OTHER INFORMATION: P4 is a hydrogen or an amino protecting group
<220> FEATURE:
<221> NAME/KEY: MISC_FEATURE
<222> LOCATION: (7)..(7)
<223> OTHER INFORMATION: P5 is a hydrogen or a sulphur protecting group

<400> SEQUENCE: 3

Xaa Xaa Gly Asp Trp Pro Cys
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is mercaptopropionic acid
<220> FEATURE:
<221> NAME/KEY: MISC_FEATURE
<222> LOCATION: (2)..(2)
<223> OTHER INFORMATION: Xaa is homoarginyl

<400> SEQUENCE: 4

Xaa Xaa Gly Asp Trp Pro Cys
1               5

<210> SEQ ID NO 5
<211> LENGTH: 4
<212> TYPE: PRT
<213> ORGANISM: Artificial Sequence
<220> FEATURE:
<223> OTHER INFORMATION: Synthetic Construct
```

```
<220> FEATURE:
<221> NAME/KEY: MISC_FEATURE
<222> LOCATION: (1)..(1)
<223> OTHER INFORMATION: P3 is a hydrogen or a carboxyl protecting group
<220> FEATURE:
<221> NAME/KEY: MISC_FEATURE
<222> LOCATION: (2)..(2)
<223> OTHER INFORMATION: P4 is a hydrogen or an amino protecting group
<220> FEATURE:
<221> NAME/KEY: MISC_FEATURE
<222> LOCATION: (4)..(4)
<223> OTHER INFORMATION: P5 is a hydrogen or a sulphur protecting group

<400> SEQUENCE: 5

Asp Trp Pro Cys
1

<210> SEQ ID NO 6
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: P3 is a hydrogen or a carboxyl protecting group
<220> FEATURE:
<221> NAME/KEY: MISC_FEATURE
<222> LOCATION: (3)..(3)
<223> OTHER INFORMATION: P4 is a hydrogen or an amino protecting group
<220> FEATURE:
<221> NAME/KEY: MISC_FEATURE
<222> LOCATION: (5)..(5)
<223> OTHER INFORMATION: P5 is a hydrogen or a sulphur protecting group

<400> SEQUENCE: 6

Gly Asp Trp Pro Cys
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: P3 is a hydrogen or a carboxyl protecting group
<220> FEATURE:
<221> NAME/KEY: MISC_FEATURE
<222> LOCATION: (3)..(3)
<223> OTHER INFORMATION: P4 is a hydrogen or an amino protecting group
<220> FEATURE:
<221> NAME/KEY: MISC_FEATURE
<222> LOCATION: (5)..(5)
<223> OTHER INFORMATION: Cys is D-Cys, P5 is a hydrogen or a sulphur
      protecting group

<400> SEQUENCE: 7

Gly Asp Trp Pro Cys
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic Construct
```

```
<220> FEATURE:
<221> NAME/KEY: MISC_FEATURE
<222> LOCATION: (2)..(2)
<223> OTHER INFORMATION: Asp is D-Asp, P3 is a hydrogen or a carboxyl
      protecting group
<220> FEATURE:
<221> NAME/KEY: MISC_FEATURE
<222> LOCATION: (3)..(3)
<223> OTHER INFORMATION: P4 is a hydrogen or an amino protecting group
<220> FEATURE:
<221> NAME/KEY: MISC_FEATURE
<222> LOCATION: (5)..(5)
<223> OTHER INFORMATION: P5 is a hydrogen or a sulphur protecting group

<400> SEQUENCE: 8

Gly Asp Trp Pro Cys
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: P3 is a hydrogen or a carboxyl protecting group
<220> FEATURE:
<221> NAME/KEY: MISC_FEATURE
<222> LOCATION: (3)..(3)
<223> OTHER INFORMATION: Trp is D-Trp, P4 is a hydrogen or an amino
      protecting group
<220> FEATURE:
<221> NAME/KEY: MISC_FEATURE
<222> LOCATION: (5)..(5)
<223> OTHER INFORMATION: P5 is a hydrogen or a sulphur protecting group

<400> SEQUENCE: 9

Gly Asp Trp Pro Cys
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: P3 is a hydrogen or a carboxyl protecting group
<220> FEATURE:
<221> NAME/KEY: MISC_FEATURE
<222> LOCATION: (3)..(3)
<223> OTHER INFORMATION: P4 is a hydrogen or an amino protecting group
<220> FEATURE:
<221> NAME/KEY: MISC_FEATURE
<222> LOCATION: (4)..(4)
<223> OTHER INFORMATION: Pro is D-Pro
<220> FEATURE:
<221> NAME/KEY: MISC_FEATURE
<222> LOCATION: (5)..(5)
<223> OTHER INFORMATION: P5 is a hydrogen or a sulphur protecting group

<400> SEQUENCE: 10

Gly Asp Trp Pro Cys
1               5
```